United States Patent [19]

Nichols, III et al.

[11] 4,211,132

[45] Jul. 8, 1980

[54] APPARATUS FOR ON-LINE DEFECT ZONING

[75] Inventors: Lee H. Nichols, III; Edmund H. Smith, Jr., both of Wilmington, Del.

[73] Assignee: E. I. Du Pont de Nemours and Company, Wilmington, Del.

[21] Appl. No.: 853,420

[22] Filed: Nov. 21, 1977

[51] Int. Cl.² .............................................. B26D 5/30
[52] U.S. Cl. .............................................. 83/71; 83/80;
83/106; 209/576; 250/563; 356/431; 364/475
[58] Field of Search .............. 209/509, 522, 576, 577;
250/563, 572; 356/200; 83/71, 371, 80, 106;
364/475

[56] References Cited

U.S. PATENT DOCUMENTS

| 3,205,740 | 9/1965 | Groves et al. | 83/371 |
| 3,246,550 | 4/1966 | Galey et al. | 83/71 |
| 3,490,147 | 1/1970 | Brichard et al. | 364/475 X |
| 3,560,096 | 2/1971 | Watson et al. | 83/371 X |

Primary Examiner—Joseph J. Rolla

[57] ABSTRACT

A non-marking type method and apparatus for optimizing the recovery, at on-line speeds, of salvageable sheet product from a large width web, utilized in conjunction with a radiation scanning type inspection system.

7 Claims, 11 Drawing Figures

SIDE-TO-SIDE

FRONT-TO-BACK

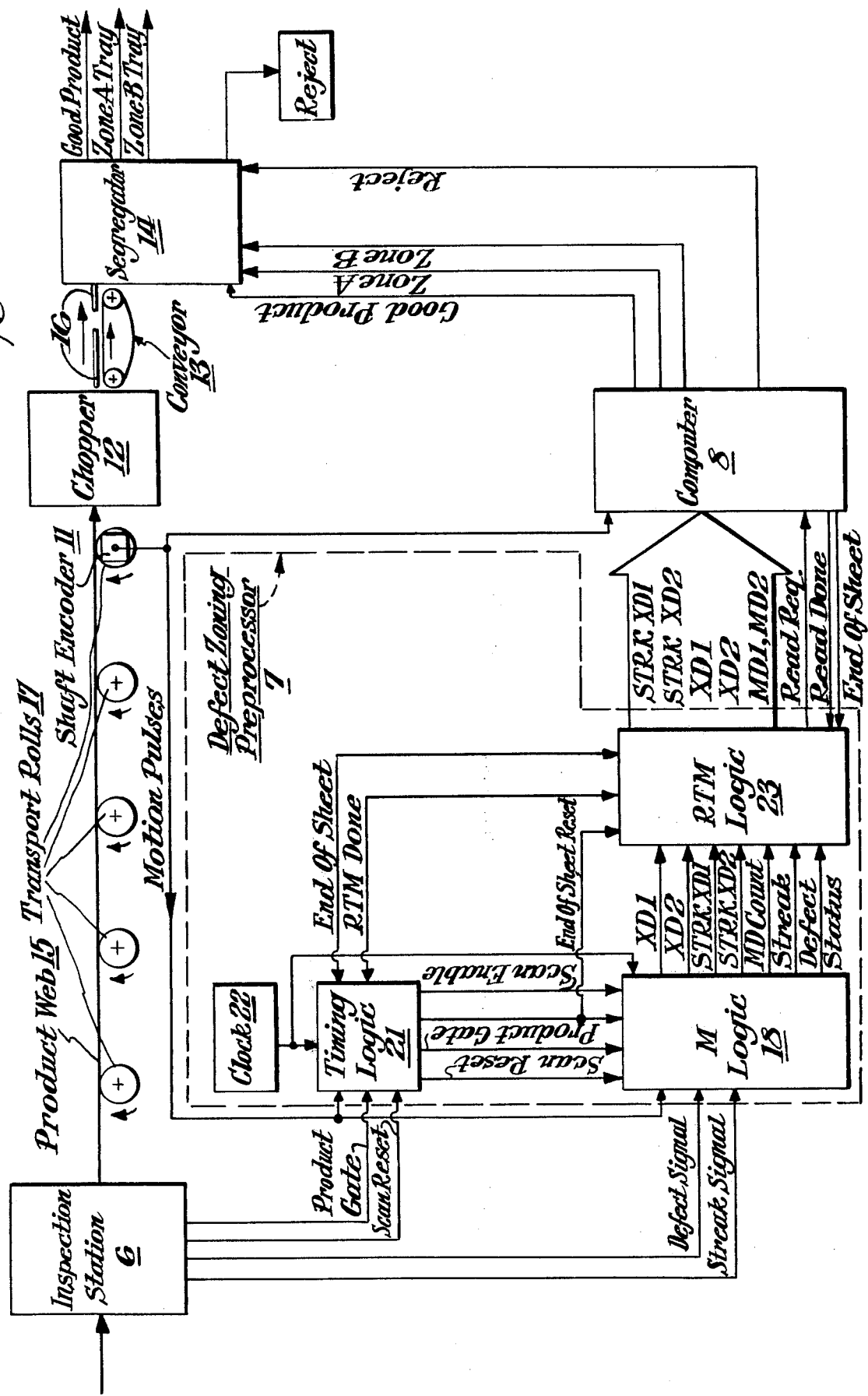

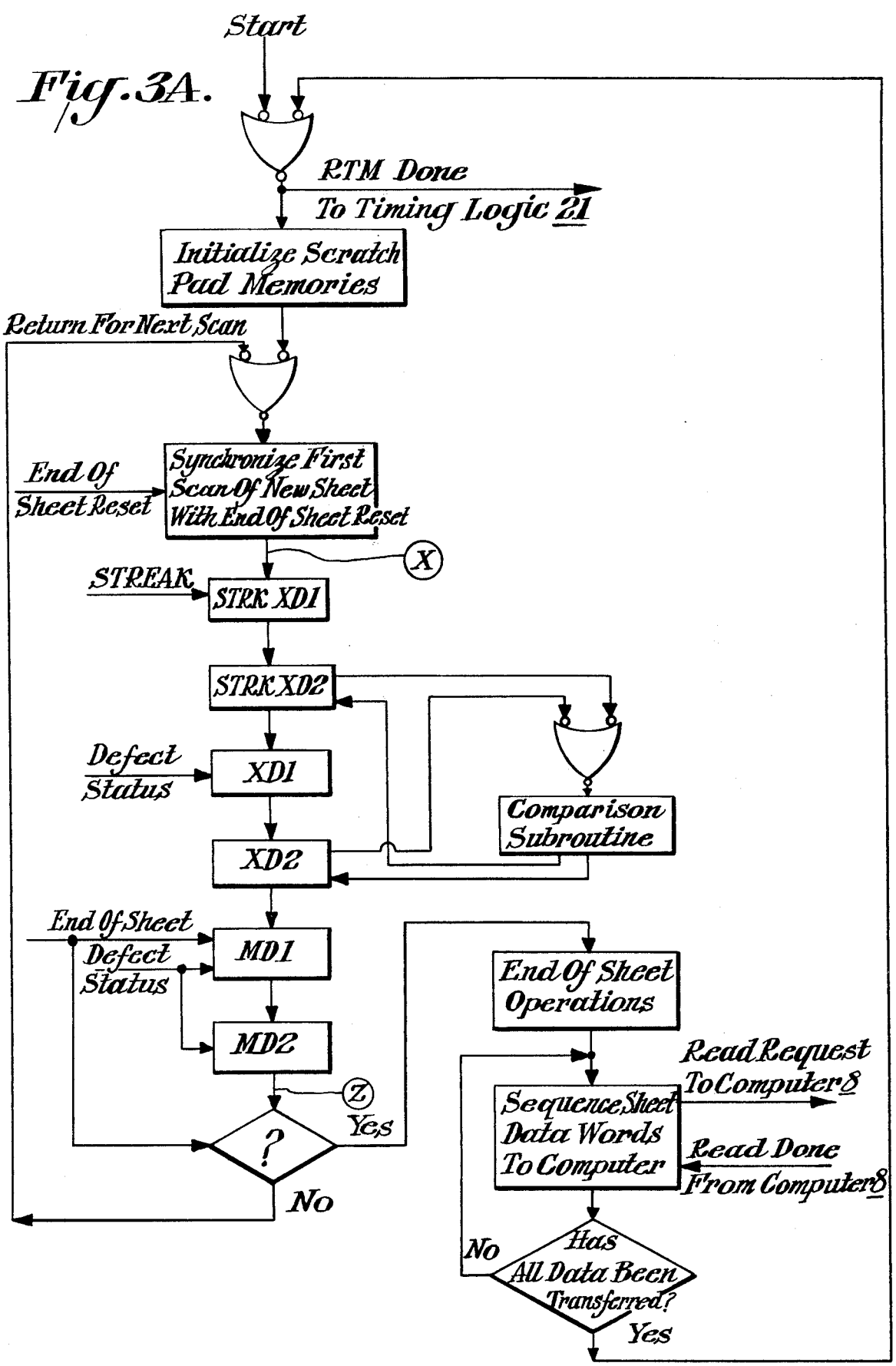

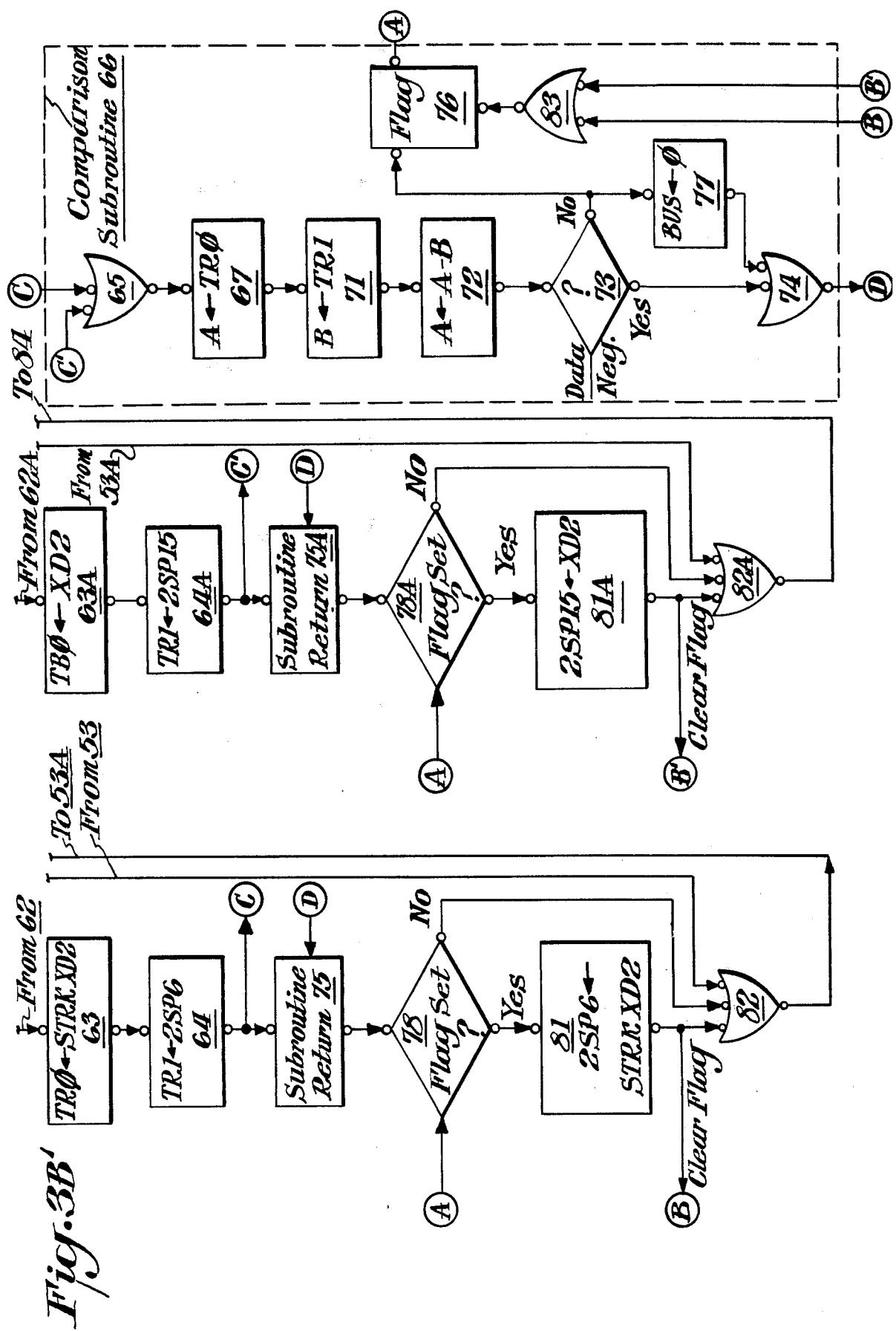

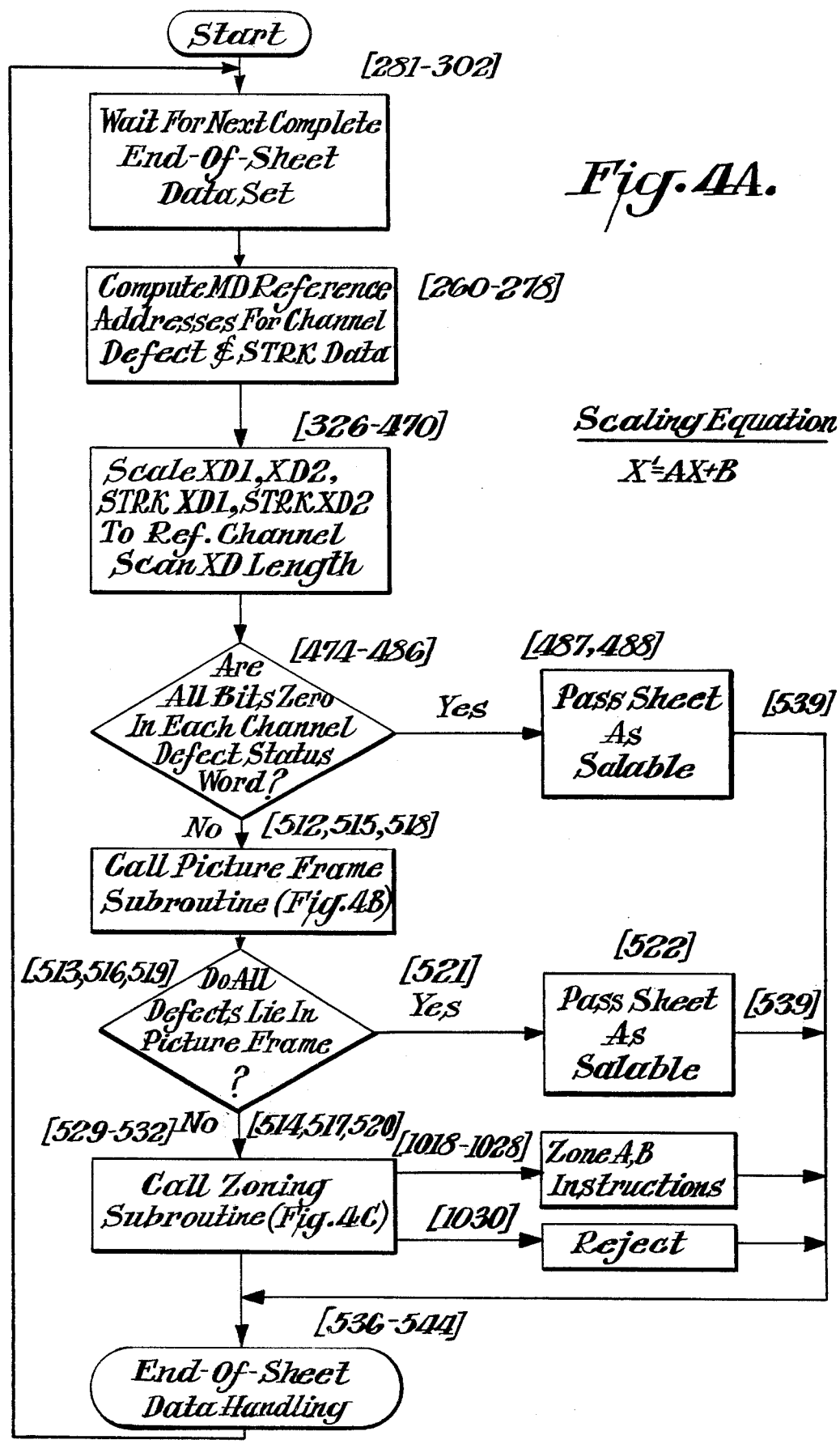

APPARATUS FOR ON-LINE DEFECT ZONING

BACKGROUND OF THE INVENTION

Although inspection systems are available which can detect and locate defects in a running product web, such as disclosed in U.S. Pat. No. 3,359,853, no systems are known which can simultaneously "zone", at on-line speeds, the defect bearing portions of the product web in such way as to maximize product yield without the need for marking the defective regions or otherwise identifying these regions once determined.

Heretofore, manual reinspection of defective product sheets has been required to determine the best way to cut the finished defective sheet when the locations, numbers and types of defects were seen visually. However, in the case of X-ray film, for example, many types of defects are difficult to see visually, making manual reinspection costly and time-consuming, thus adversely affecting the rate at which product can be released for sale.

Indeed, in the course of manual reinspection, frequently entire sheets containing salvagable regions would be discarded in order to expedite production. For high unit cost products, such practices are obviously intolerable. An object of this invention is to provide a method and means to reduce this waste and enhance product yield.

BRIEF SUMMARY OF THE INVENTION

This invention comprises a computer system defect zoning preprocessor circuit comprising a clock, a series of counters and a combination of digital logic elements designed to operate on the defect-related logic pulse discriminator output signals produced by a linear scan inspection system together with the motion pulses from an associated shaft encoder to form hypothetical XD (transverse) and MD (machine direction) oriented boundaries around the smallest rectangularly-shaped region in each inspected sheet which contains all detected defects. Using the boundary information as input, and by means of a zoning algorithm, a computer is programmed to select the best cutting or segregating strategy from those specified at the outset and then produce orders with appropriate delays, to the stacker or segregation apparatus disposing of the sheet, before the next sheet passes through the inspection station.

RELATED PATENT APPLICATION

The product quality inspection method and apparatus used in conjunction with the zoning invention of this application is the subject matter of Application Ser. No. 853,421 filed of common data herewith.

THE DRAWINGS

FIG. 1 is a schematic representation of a typical defect-bearing sheet showing the size and location of the smallest XD, MD oriented rectangle containing all of the defects, FIGS. 1A-1D are schematic representations of four typical zoning patterns which are used to reduce a sheet-sized portion of a product web to finished product size, FIG. 2 is a schematic assembly representation of a preferred apparatus of this invention, FIG. 3 is a detailed circuit diagram showing the M logic defect location section 18 of the defect zoning preprocessor 7 circuitry of FIG. 2, FIG. 3A is a schematic of the general layout of the RTM logic section 23 of the defect zoning preprocessor 7, of FIG. 2, FIGS. 3B and 3B' in vertical extension constitute a detailed RTM logic circuit diagram showing the system used to generate XD and MD data for the computer, FIGS. 4A-4C are flow charts detailing the computer algorithms used to generate appropriate sheet zoning orders, and FIG. 4D is a pictorial representation of a picture frame concept employed in product grading.

DETAILED DESCRIPTION

Before describing the details of the invention, the following is a brief summary of what the invention accomplishes.

Figure 1:
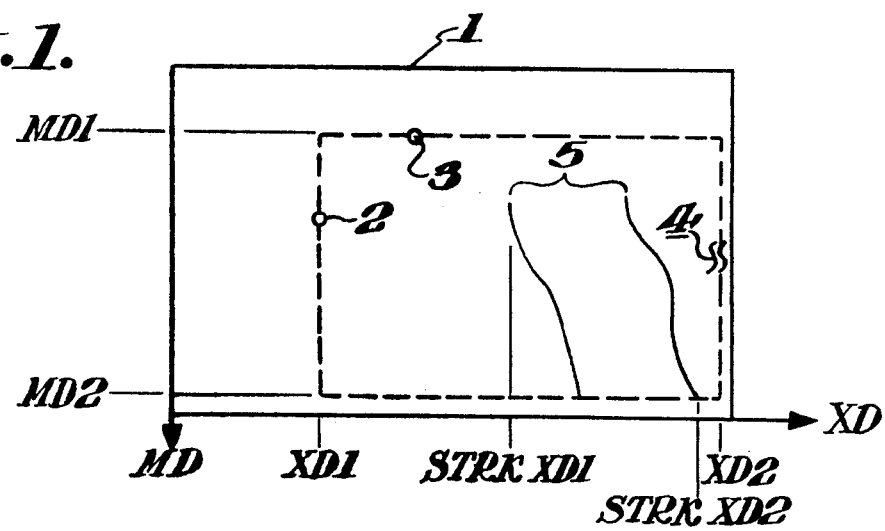

FIG. 1 is a representation of a severely defective product sheet 1, in which a scanning type inspection system has previously determined the existence of two small spotsized flaws 2 and 3, a pair of hair-like flaws noted generally by 4 and a broad streak type defect 5. In the description, the transverse (XD) coordinates run across the sheet from left to right and the machine direction (MD) coordinates run from top to bottom. Moreover, the first scan to encounter a defect is labeled MD1 and the last scan to see a defect, such as streak 5, is labeled MD2. Simultaneously, the defect zoning apparatus separately tallies the XD locations of the leading and trailing edges of streak 5 and discrete defects 2, 3 and 4, so that, by the time the last scan crosses the sheet, XD1 and STRK XD1, define the transverse location of the leftmost discrete defect or streak edge, respectively, and XD2 and STRK XD2 define the rightmost edges of these defect classes. The smaller of XD1 and STRK XD1 is used with the larger of XD2 and STRK XD2 to define the limits of the dashed rectangle enclosing all the defects.

FIGS. 1A-1D show four typical zoning patterns which can be used to salvage the non-defective portions of a sheet, namely: side-to-side zones A and B and front-to-back zones A and B. These front-to-back and side-to-side zoning pattern groups, respectively, specify the orientation of the horizontal and vertical cut lines. Should the front-to-back zoning mode be selected, the defect zoning system will disregard STRK and DEFECT XD information and make a decision whether to salvage the sheet according to horizontally oriented zone pattern A or zone pattern B, based on MD data only. On the other hand, should the side-to-side zoning mode be selected, the salvaged sheet will be zoned according to the vertically oriented zone patterns A or B by disregarding the MD data and basing zoning decisions strictly on DEFECT XD and STREAK XD information. Although not shown, zoning patterns including both horizontal and vertical cutting lines might be used as well. Severely defective sheets, such as illustrated in FIG. 1, to which perhaps no zoning patterns pertain, are rare in the manufacture of X-ray film. Rather, the majority of defects are grouped within the sheet such that segregation of the defective product into one or more of the FIGS 1A-1D zones is practicable. Cut lines SX1, SX2, SM1 and SM2 and the number of zoning combinations used for any given application are selected as a function of such factors as final product size, quality and cost per unit sheet. Furthermore, the horizontal and vertical cutting lines are oriented with respect to the sheet edges to facilitate chopping operations in the packing area of manufacture.

FIG. 2 is a block diagram of the defect zoning system which comprises the following essential components: a web inspector located at an inspection station 6, a defect zoning preprocessor 7, a computer 8, and a shaft encoder 11. Chopper unit 12, conveyor 13, and segregator 14 operate as an integral unit to cut and dispose of product web 15, transported by rolls 17, into sheets 16 of predetermined size, by means such as described in U.S. Pat. No. 4,041,816 issued Aug. 16, 1977, the property of common assignee, and then transfer the chopped sheets into one of several collection trays for packing, further cutting or for rejection in accordance with zoning instructions received from computer 8. Details of the operation and design of the latter three components (i.e., the chopper unit 12, conveyor 13 and segregator 14) are outside the scope of the invention and will, therefore, not be further discussed herein.

An inspection system, such as that described in U.S. Pat. No. 3,843,890, operates at inspection station 6 to produce logic level signals indicating the presence of defects on the product web and transmits these signals to defect zoning preprocessor 7. Inspection system discriminators normally produce the defect signals in logic level format in order to facilitate recording, perhaps as a function of position of the web, by means such as a computer memory or teletype (not shown). Furthermore, the inspection system may use several discriminators to detect different classes of defects, such as streaks, holes, and thick spots. FIG. 2 shows two of these logic level discriminator outputs, namely: streak and defect signals, which are inputted directly to the M logic section 18 of preprocessor 7. In addition, the inspection system normally generates gating and timing signals; two of these, the product gate signal and the scan reset signal, as described further in U.S. Pat. No. 3,843,890, supra, are input to the timing logic section 21 of preprocessor 7. The third input to timing logic section 21 is produced by shaft encoder 11, typically a Teledyne-Gurley Model 8625. Shaft encoder 11 is geared directly to a transport roll 17 and produces motion pulses at a rate directly proportional to web velocity. Assuming that running product web 15 is maintained under constant tension, a single shaft encoder may be used to furnish motion pulses for both MD scan position-keeping performed in M logic section 18 and to provide computer 8 with the basis it needs to calculate an end of sheet data word.

The heart of the defect zoning system of the invention is defect zoning preprocessor 7. This component comprises four major sections, namely: a 5 MHz high frequency digital clock 22; timing logic 21; M logic section 18 and RTM logic section 23. All signal paths shown interconnecting these sections convey logic level binary data. Furthermore, the data transmitted to or from RTM logic section 23 pass through RTM M7311 general purpose parallel I/O interface units (not shown) to transmit them at prescribed times to the receiving circuitry for processing.

More specifically, clock 22 generates a digital pulse train as input to M logic section 18 of sufficient pulse repetition rate and pulse duration to resolve the XD locations of the digital events passed to it from inspection station 6. On a second path the timing signal from clock 22 passes to timing logic section 21. Timing logic section 21 consists of various logic elements which are arranged in ways familiar to persons skilled in the art to produce the control signals necessary to start and stop the scan and sheet calculations generated in M logic section 18 and RTM logic section 23, respectively, and to synchronize their operation in such a way as to ensure that only valid and consistently timed data are transferred between these two sections and computer 8.

Figure 3:
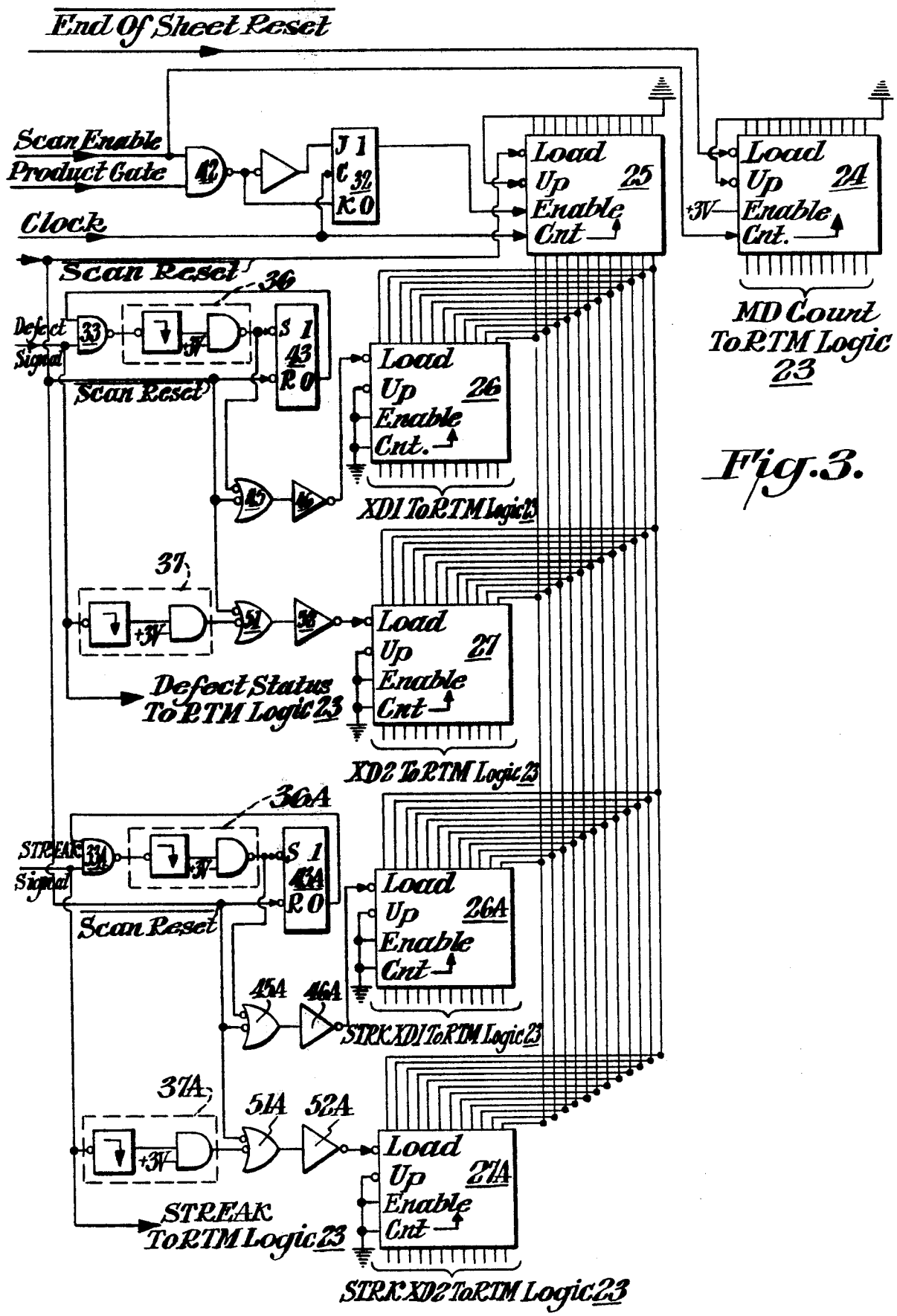

One of the outputs from timing logic section 21 is the scan enable signal. It is formed by logic means synchronizing the motion pulse occurrences from shaft encoder 11 with the occurrences of a product gate signal from inspection the occurrences of a product gate signal from inspection station 6 and a clock pulse from clock 22. The M logic section 18 then uses the scan enable signal thus generated to increment MD couter 24 (FIG. 3) according to product distance travelled, so that regardless of either scan rate or web velocity variations, the MD separation between scans will remain constant. (In some embodiments it may be desirable to process data from every scan and use scan enable pulses solely to increment MD counter 24.) The scan enable signal is also used to enable master XD counter 25 (FIG. 3).

A second output produced by timing logic section 21 is the end of the sheet reset signal. This signal is generated after the accumulated sheet data has been sent to computer 8 and RTM logic section 23 has sent out an RTM DONE signal (FIG. 3A) to indicate all data processing operations performed by defect zoning preprocessor 7 on the sheet data have been completed. The end of sheet reset signal initializes MD counter 24 (FIG. 3) of the M logic section and also is used to synchronize the RTM logic section 23 operations with the first scan of the next sheet as shown in FIG. 3A.

The last two signals transmitted from timing logic section 21 to M logic section 18, namely: scan reset and product gate, hereinbefore mentioned, originate in the inspector 6. Scan reset is triggered by a separate end-of-scan photocell, whereas the product gate signal is formed by logic circuit means upon discriminating the leading and trailing edges of the signal as each scan passes across the product web. Methods for forming these two signals are well known in the art (refer U.S. Pat. No. 3,843,890 supra). Next, it is shown how these signals are used in connection with the operation of M logic section 18.

The third major component of defect zoning preprocessor 7 is M logic section 18. This section contains the counting, gating, and addressing logic elements which operate to provide to RTM logic section 23 both instantaneous and cumulative XD and MD locational data on a scan-to-scan basis. FIG. 3 details the means used to produce the following set of zoning signals as output to RTM logic section 23: MD count, XD1, XD2, streak XD1 (STRK XD1) and streak XD2 (STRK XD2), and both streak and defect scan status indicators. Referring to FIG. 3, master counter 25 produces a series of location pulses on output data lines connected to slave counters 26, 27, 26A and 27A, operated as registers, as incremented by clock pulses from clock 22 and as controlled by JK flip-flop 32. Flip-flop 32 remains active through each enabled product scan, as ensured by NAND gate 42. Upon receipt of a defect pulse at an input terminal of NAND gate 33, provided it is the first defect to be detected in the scan, pulse generator 36, connected to the output terminal of NAND gate 33, initiates a short pulse through OR gate 45 and inverter 46 to the load input terminal of counter 26 to sample the address location data input from master counter 25.

Also connected to the output of pulser 36 is the set terminal of flip-flop 43 whose output terminal is connected to the second terminal of NAND gate 33 and whose reset terminal receives the scan reset signal from timing logic section 21 (FIG. 2) at the end of each scan. Thus, by this means, counter 26 records only the XD location of the first edge of the first defect detected on each scan (XD1) and retains that count until it is reset before the next scan by the scan reset signal. The scan reset signal not only initializes master counter 25 but also clears each of the slave counters 26, 27, 26A and 27A.

In contrast to the circuitry used to develop the XD1 data, the trailing edge of each of the defect pulses in a given scan causes pulse generator 37 to produce a corresponding short pulse through OR gate 51 and inverter 52 to the load terminal of counter 27. Thus counter 27 generates an updated XD2 coordinate for the trailing edge of each defect seen during each scan for transmission to RTM logic section 23.

Figures 1A, 1B:
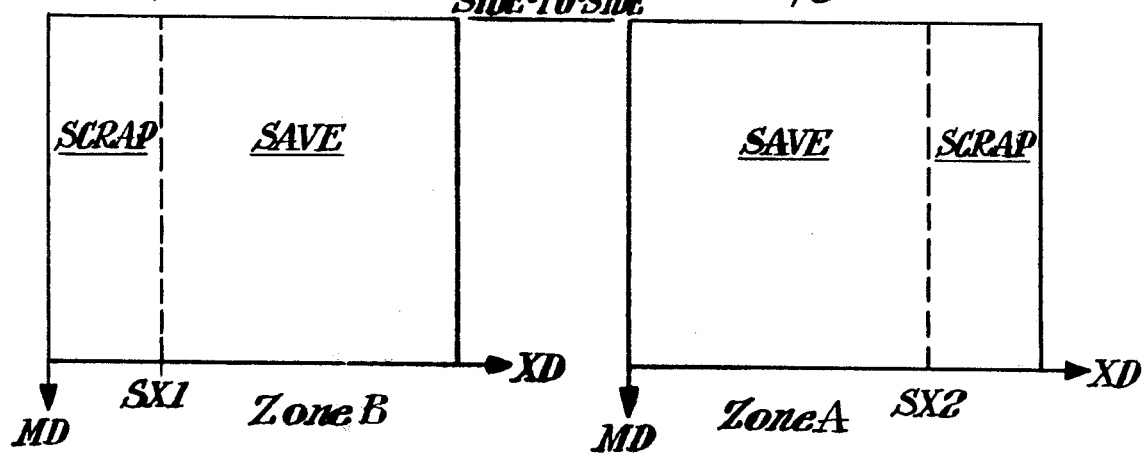
Figures 1C, 1D:
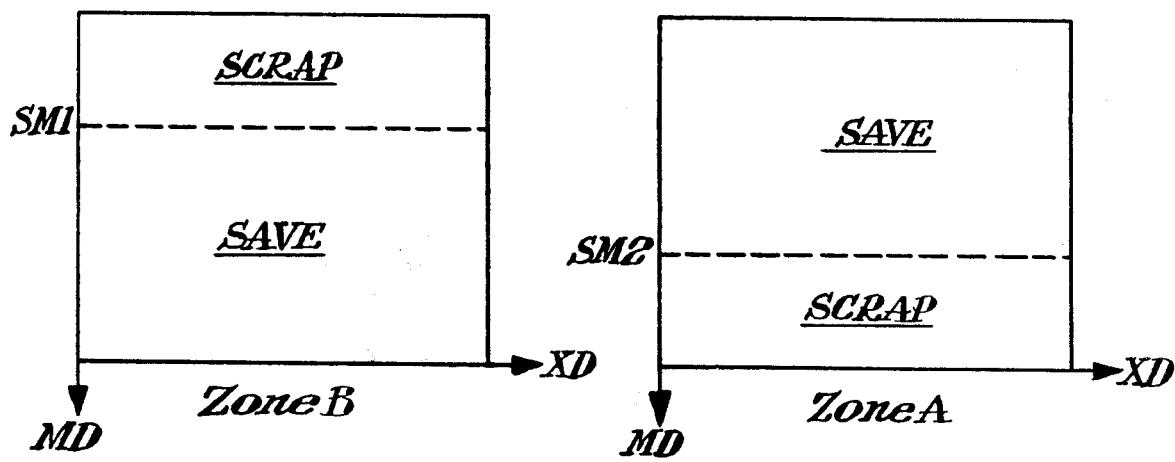

The operation and design of the circuitry containing counters 26A and 27A for the generation of STRK XD1 and STRK XD2 information is identical to that used to generate the XD1 and XD2 data. The reason for distinguishing between the XD1 and STRK XD1 and their XD2 circuit counterparts is to be able to apply separate zoning criteria for the streak condition which takes into account possible undetected excursions of streak diffuse edge signals across zoning pattern cut lines (FIG. 1A). A means for doing this is hereinafter described.

Figure 3B:
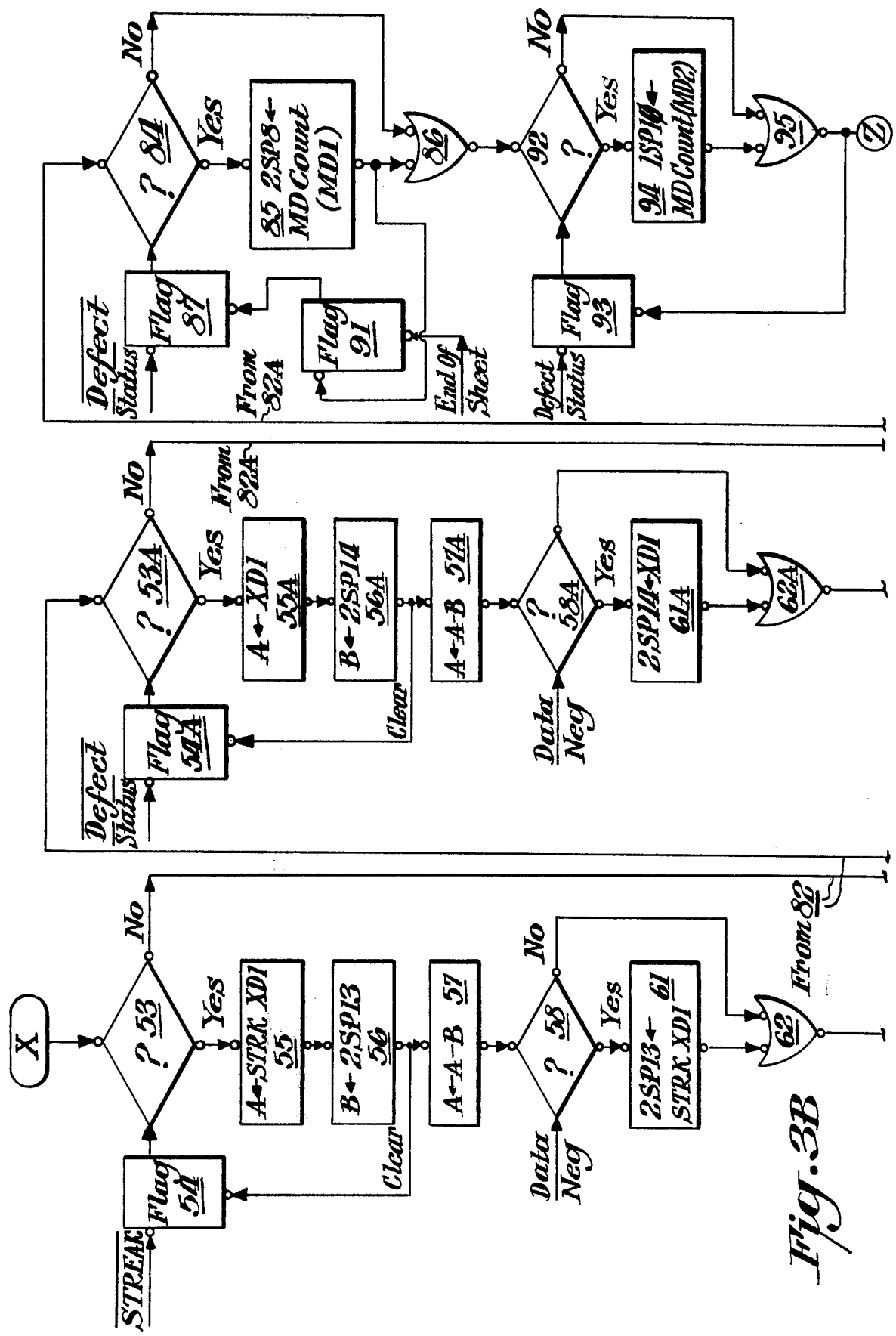

The fourth and final component of defect zoning preprocessor 7 is RTM logic section 23. Referring to FIGS. 3A and 3B,3B′, this circuitry comprises a logic system of register transfer modules (RTM) marketed by Digital Equipment Corporation. These elements are arranged to collect and process the various XD and MD defect-related sheet boundary data for transmission to computer 8 (FIG. 2) at the end of each sheet. This data transfer occurs upon each end-of-sheet signal generated by computer 8 marking each instant the tally of motion pulses from shaft encoder 11 reaches a prescribed number corresponding to the sheet MD dimension. Generation of each end-of-sheet signal by computer 8 is used by timing logic 21 to ensure that data transfer does not take place during a scan. A distinguishing feature of the RTM logic system is its ability to calculate and accumulate the event location data the computer needs to determine the location and size of the defective region within each scanned sheet-sized portion of the product web in real time. The representation of FIG. 3A is a flow chart showing, in abbreviated form, the arrangement of RTM modules into two concentric feature processing loops. The inner loop comprises the scan tasks for determining the following information in each inspected sheet:

the smallest STRK XD1 value
the largest STRK XD2 value
the smallest defect XD1 value
the largest defect XD2 value
the location of the first scan (MD1) to encounter a defect and
the location of the last scan (MD2) to encounter a defect.

The outer loop, on the other hand, comprises the end-of-sheet tasks such as sequentially interrogating the scratch pad memories, where the XD and MD data are stored, and transmitting this data to computer 8 via RTM M7311 General Purpose parallel I/O interface units (not shown). A read request signal produced in this loop by the RTM section is used to tell computer 8 that a data word is ready for transmission, whereas a read-done signal, generated by computer 8, informs the RTM section when it has completed reading the data into its registers.

A detailed description of the functions and design considerations for the use of RTM modules in the loops shown is outlined in Bell, Grayson and Newell "Designing Computers and Digital Systems", Digital Press, 1972, as developed by the Digital Equipment Corporation.

FIGS. 3B, 3B′ constitute a detailed RTM circuit diagram of the assembly of blocks between points X and Z of FIG. 3A showing the means used to generate STRK XD1, STRK XD2, XD1, XD2, MD1 and MD2 sheet data.

After synchronization of the initial scan with the occurrence of an end-of-sheet reset signal, which occurs upon entry of the next sheet-sized portion of the web into the inspection station, program control passes to the data input terminal of an M7312 two-way branch module 53. The condition terminal of branch 53 is connected to the output of an M7306 flag module 54. Upon the occurrence of a streak signal, flag module 54 switches program control from the normal bypass route to a path through evoke modules 55, 56 and 57. Evoke module 55 then causes the STRK XD1 counter 26A (FIG. 3) contents to be loaded into register A of the arithmetic and logic unit, modules M7301 and M7300 respectively (not shown) and evoke module 56, connected to the output of evoke module 55, causes the most recent STRK XD1 count value, which has been stored in scratch pad memory number 2 word 13 (2SP13), to be loaded into register B. [A scratch pad memory M7318 is a 16-word by 16-bit random access memory (RAM) organized to operate as 16 independent 16-bit registers. In this case, the contents of the 13th register (word) is loaded into register B of the M7301/M7300 module pair.]

When this step is complete, program control clears flag 54 and enters evoke module 57, which is connected to the output of evoke module 56. Evoke module 57 causes the difference value (A−B) formed in the M7300/M7301 module pair to be loaded into this module's register A. Should this difference be negative (i.e., the instant STRK XD1 value is smaller than the previously calculated STRK XD1 value) a bus monitor and terminator module M7332 (not shown) will cause a logic one input signal to be applied to the condition terminal of two-way branch module 58. [A bus monitor and terminator module M7332 is used to detect whether the last data transferred on the RTM data bus was less than zero, i.e., negative. If it was, a logic high output signal is produced via the DATA NEG(ative) terminal, which is connected to the left-hand tip of two-way branch 58 to direct program control into the appropriate YES path.] In this event, evoke module 61 orders the new STRK XD1 value to be loaded into scratch pad memory 2 (2SP13); otherwise the former STRK XD1 value remains unchanged. Similarly, sheet defect XD1 data from counter 26 (FIG. 3) is processed to obtain a minimum XD1 value through the action of corresponding RTM components 53A, 54A, 55A, 56A, 57A, 58A and 61A.

After program control passes through OR gate 62, the next task is to compute the maximum value of sheet STRK XD2. Evoke module 63 (FIG. 3B') causes the STRK XD2 data of counter 27A (FIG. 3) to be loaded into an M7305 transfer register module zero location (TR$\phi$), while evoke module 64 causes the contents of 2SP6 (i.e., the largest value of STRK XD2 yet computed on the scan) to be loaded into the transfer register one location (TR1). With these data, program control enters terminal Ⓒ of OR gate 65 (FIG. 3B') in comparison subroutine section 66, shown on the right-hand side of FIG. 3B', to determine which of the two STRK XD2 values is the larger. Evoke module 67 connected to the output of OR gate 65, causes the contents of TR$\phi$ (containing the instant STRK XD2 data) to be loaded into register A of arithmetic and logic function module pair M7300/M7301, whereas evoke module 71 connected to evoke module 67, loads the contents of TR1 into register B. When this step is complete, evoke module 72 connected to evoke module 71, causes the difference value (A-B) formed in the M7300/M7301 module pair to be loaded back into register A. Should this difference be negative (i.e., the instant value of STRK XD2 is smaller than the previously calculated STRK XD2 value), a bus control and terminator module M7332 (not shown) will apply a data negative signal to the condition input of two-way branch module 73, connected to the output terminal of evoke module 72, which directs program control through OR gate 74 back to the main program at point Ⓓ of an M7315 subroutine return module 75 (third block from the top, left-hand sequence, FIG. 3B'). On the other hand, should the result be positive or zero, program control causes flag module 76 to set a flag condition A on two-way branch 78 while it causes evoke module 77 to enter zero onto the RTM data bus before exiting comparison subroutine 66 through OR gate 74.

Next, dependent on the status of flag 76, two-way branch 78, which is connected to the output terminal of subroutine return module 75, will direct program control either to load the new STRK XD2 value into 2SP6 by means of evoke module 81 or to bypass this step and exit through OR gate 82 to the defect XD1 and XD2 computation task at the top of FIG. 3B. Incidentally, as program control passes through evoke module 81, it will also clear flag 76 in comparison subroutine 66 on a path through OR gate 83 with entry at point Ⓑ. Defect XD2 data is processed similarly through corresponding components 62A, 63A, 64A, 75A, 78A, 81A and 82A with the aid of comparison subroutine 66 through corresponding entry and exit points.

The last RTM task generates defect MD1 and MD2 location values. Two-way branch 84 (FIG. 3B) is connected to the output of OR gate 82A (FIG. 3B') and directs program control to either evoke module 85 or on a bypass around it to OR gate 86 dependent on the status of flag 87. The input terminal of flag 87 is connected to the defect status line from M logic section 18 (FIG. 2) with its output terminal connected to the condition input of two-way branch 84. Flag 91, having its input terminal connected to the output of evoke module 85 and its reset terminal connected to the end-of-sheet signal line from computer 8 (FIG. 2), has its output connected to the reset terminal of flag 87. This circuit ensures that evoke module 85 only asserts reading the MD count from counter 24 (FIG. 3) into 2SP8 for the first scan seeing a defect in the new inspected sheet. As program control passes to two-way branch 92, the presence of a defect status signal at the input to flag 93 will cause evoke module 94 to load the instant count (MD2) from counter 24 (FIG. 3) into 1SP1$\phi$ (and for each succeeding scan seeing a defect in the sheet, since reset for flag 93 is immediate). OR gate 95 conveys program control to exit Ⓩ (FIG. 3A) regardless of the path taken from brnach 92.

DEFECT ZONING ALGORITHMS

After defect zoning preprocessor 7 accumulates the zoning data from a frame of scans, and upon receiving an end-of-sheet command, it transmits this data set to computer 8 before the next sheet-sized portion of the web passes through the inspection station. Zoning algorithms, such as those shown in the flow sheets of FIGS. 4A-4C then direct the computer to (1) scale and adjust XD and MD data values from the several inspection locations to be consistent with the physical sheet boundaries, (2) determine whether XD1, XD2 and STRK XD1, STRK XD2, and MD1, MD2 data pairs define defect conditions within an allowable picture frame border, (3) determine how to cut the defective sheets to maximize yield, given a number of preselected cutting patterns, and (4) issue appropriate product acceptance, zoning or reject commands.

Figure 4B:
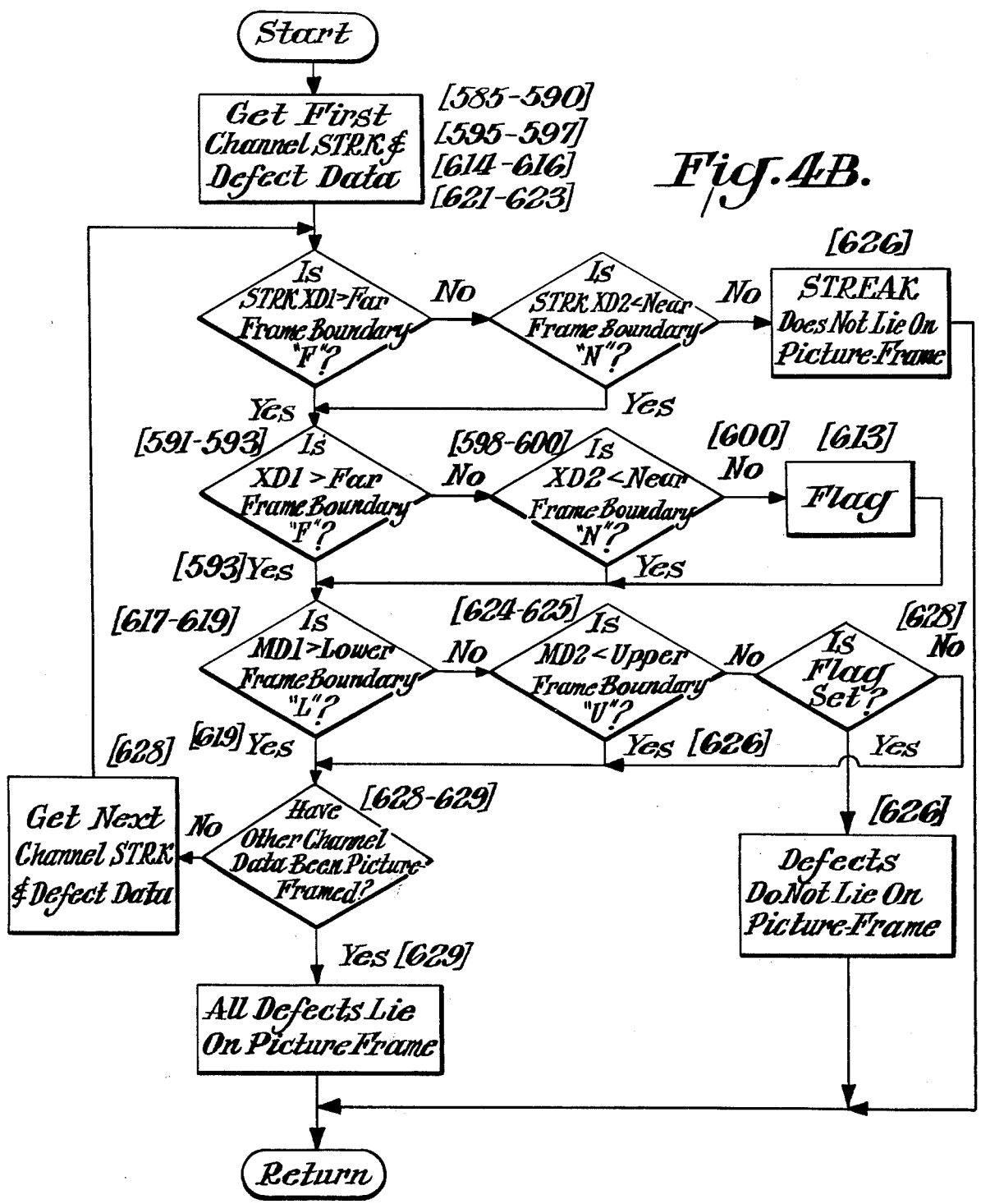
Figure 4D:
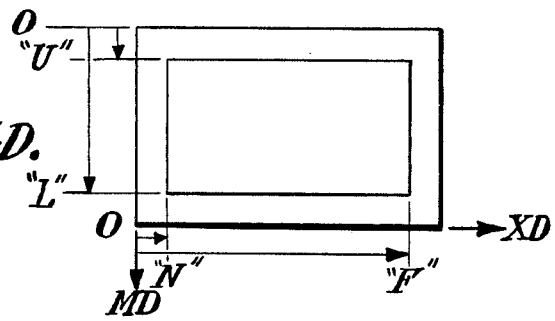
Figure 4C:
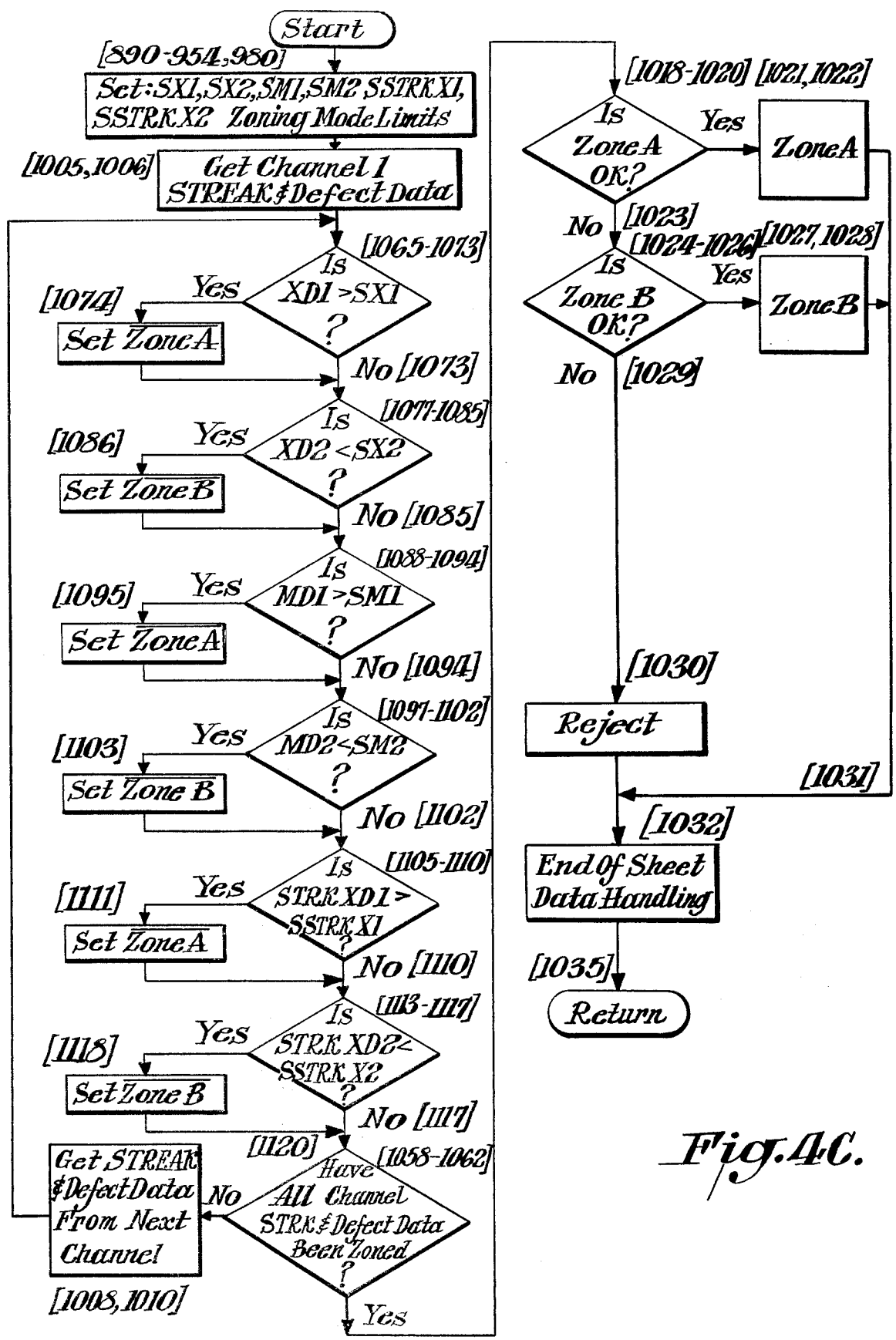

While steps are outlined generally in FIG. 4A, FIGS. 4B and 4C provide greater detail covering the picture-framing and zoning steps, respectively.

Turning now to FIG. 4A, assuming that the picture frame border dimensions and zoning pattern XD and MD dimensions have already been entered from off-line, and from passage of product web 15 through the inspection station 6, computer 8 will compute corrected MD1 and MD2 counts, referenced to the bottom (or trailing) edge of the inspected sheet, from the MD count data received from RTM logic section 23 upon each end-of-sheet data transfer (FIGS. 2, 3A, 3B). Assuming a constant line speed between stations, and assuming the MD distances between chopper 12 (FIG. 2) and the inspection channels at inspection station 6 are known, this MD count adjustment is simply an additive constant.

The first two steps compensate the channel data for inspection station interchannel MD count adjustment and scan geometry XD differences, including those associated with path length and scan spot velocities. [In the event that multiple inspection channels are used at an inspection station 6, there will be a certain fixed MD separation between them. The value of this fixed interchannel spacing (in motion pulses) with respect to a reference channel scan line is what computer 8 applies to a particular inspection channel MD count data. This action is represented by the "Compute MD reference" block of FIG. 4A.] The algorithm applies a linear equation scaling factor of the form $X'=AX+B$ (FIG. 4A) using the XD count data received from a reference inspection channel, to scale the XD data of the remaining channels accordingly. Such a scaling factor is easily programmed (refer lines 325-470, program listing, Application Ser. No. 853,421). As a consequence of XD linear scaling and MD count adjustment, sheet XD and MD data, as generated by independent inspection channels, is brought into agreement with a standard set of coordinates.

The next step determines whether either streak or defect data was generated by any one of the inspection channels. (In this connection, a no-defect condition may be indicated by all zero bits in all of the channel defect status words formed in computer 8 which are used to represent the source of each channel's RTM data input.)

Assuming a defect is present, a picture frame subroutine (FIG. 4D) is called upon to determine whether the flaw appears on the peripheral border region of the sheet, and, if so, pass the sheet as salable. This is usually a practical preliminary step in product manufacture, since handling operations preliminary to cutting to final size and packaging usually affect the quality of the edge of the precut sheet.

Referring to the flow chart of FIG. 4B, and the sketch at FIG. 4D, each set of XD and MD channel data is sequentially compared with its respective near "N", far "F" and upper "U", lower "L" picture frame values to determine at an early stage the need for additional product segregation action before the sheet is packaged as good product.

Finally, assuming some of the sheet XD and MD RTM generated values are in the "picture" area, the flow chart of FIG. 4A calls for the zoning subroutine of FIG. 4C to select the appropriate cutting pattern of those defined beforehand (i.e., those of FIG. 1A). [In elaboration, the purpose of the picture-framing routine is to segregate the inspected sheets having defects along their edges from those having defects within their central enclosed areas. In manufacturing, where transferring finished sheets from the segregator to the cutting apparatus is done manually, the edges of the sheets normally receive the most handling. It is therefore to be expected that additional defects can be introduced onto the sheet during this operation, but, due to their peripheral locations, these are of a nature not affecting the end use. Consequently, defects which inspector station 6 locates within the peripheral region of the sheet (i.e., within the picture frame border edge and side limits defining the central region of the frame) are not disqualifying.] Referring to FIG. 4C, and with the aid of FIG. 1A, the initial step specifies the zoning mode which is to be used, namely: (1) the side-to-side mode with vertical cut lines SX1 and SX2 corresponding to zoning patterns B and A, respectively, or (2) the front-to-back mode with horizontal cut lines SM1 and SM2 corresponding to zoning patterns B and A, respectively. S STRK X1 and S STRK X2 cutting locations (not shown) have been separately specified, using cut line locations SX1 and SX2 as bases, to provide for the possibility that the streak detector may fail to discriminate the start of a gradual, diffuse edge condition at the instant the scan passes over it. The result of this action would be the appearance of part of a streak on the saved portion of a zoned sheet. Consequently, we have made the streak cut lines S STRK X1=XS1+$\Delta$ and S STRK X2=SX2−$\Delta$, where $\Delta$ might be of the order of 5 mm. [The values of S STRK X1 and S STRK X2 are set out in the table of defined zoning limits as SK1 and SK2, respectively, at lines 869-954 of the quality screening and zoning algorithm in the appended program printout. The offset, $\Delta$, appears as the difference between the tabulated SK1, XD1 and SK2, XD2 values, respectively.] After sequentially comparing the XD and MD channel data of each inspection channel with the particular chopping coordinates specified by the zoning mode, the algorithm determines whether to use zoning pattern A or B, or none at all. Dependent upon whether front-to-back MD zoning or side-to-side XD zoning has been selected, a zone A instruction corresponds to sheet size reduction along either SX2 or SM2 lines, whereas a zone B instruction corresponds to sheet size reduction along either SX1 or SM1 lines. Then, the end result, after all inspection channel data have been thus compared, is that the algorithm has determined automatically either: (1) sheet rejection, or (2) product cutting instructions according to the predetermined zoning specification in order to maximize finished product recovery.

Although RTM logic elements have been used to compute the zoning information as detailed above, a microprocessor, or several microprocessors operating in parallel, can be arranged to produce similar results by persons skilled in the art.

COMPUTER PROGRAM

The appended program listing is incomplete in some relatively unessential respects as regards full conformance with the flow charts of FIGS. 4A–4C, inclusive, to which it is cross-referenced by the bracketed program line numbers drawn in adjacent the several blocks of the flow charts. For example, some detailed steps, such as the pickup of the inspector channel word for the first channel, combining it with the second and third channels to make a combined status word, is not illustrated in the flow charts, in the interests of brevity of the showings.

The following brief interpretation of the program sequence is provided to assist the reader's understanding, all references being in the chronological program pages and lines, thus, Page 15, lines 87 through 120—A listing of twenty-nine typical sheet features, one or more of which can be used as the basis for zoning pursuant to this invention.

Page 16, lines 131-145—The packed channel defect status word bit locations for seven common X-ray film defect classes are set out here.

Page 17—Remarks applicable to Quality Analysis (QUAL) for a 3-channel inspection apparatus.

Page 19, lines 260-278—Execution of program starts with MD count adjustment.

Page 19, lines 281-304—Shows steps needed to make valid data check (not shown in Flow Charts).

Page 20, lines 310-323—Composition of 3-channel defect status word.

Page 20, line 335, through page 24, line 470—Scaling procedures QUAL 4 through QUAL 4D adjust the XD data to make it line up with the product.

Refer to FIG. 4B in conjunction with top of page 25 et seq. of the listing

Page 25, lines 504-544—QUAL 5 through QUAL 7 Routines—Check for small defects in the picture frame area (shown disabled in the listing). QFIN, line 541, is the completion of quality classification. By line 521 it is determined whether one can "picture frame" or not.

Page 26, lines 555-576 GETDAT-PUTDAT—Two service routines to get input data from the buffer, apply an address offset to the data, then return it to the buffer at the offset address location.

Page 27, line 585. QUAL S1—Transverse direction subroutine.

Page 27, line 602, QUAL SA—Length of defect ascertainment.

Page 27, line 613, QUAL SB—Machine direction subroutine.

Refer to FIG. 4C in conjunction with top of page 29 et seq. of the listing

Line 691, START 2—By this line the sheet data operations are finished.

Pages 30 and 31—Zoning patterns are shown, the cross dimensions corresponding to final product XD cut lines whereas the vertical lines correspond to the MD product cut lines.

Page 32—The normal limits of the several data values to be compared are tabulated at lines 826 through 841, with corresponding measurement resolution at lines 845-849.

Pages 33 and 34—Zoning Limit Data Tables. Lines 891-953 comprise the prestored data defining the cut line dimensions corresponding to comparison Codes 1 to 7.

Page 35, line 975—Starts zoning task.

Page 35, line 986—Identification of the zoning parameters selectable by operator.

Page 35, line 988—SHSTAT (sheet status word) equivalent to the composite individual defect status words.

Page 35, line 991—Ascertainment of presence of defects which cannot be handled.

Page 35, lines 996-1003—With small defects, picture frame boundary can be relaxed (not shown in Flow Chart).

Page 37, lines 1038-1057—Zoning subroutine remarks.

Page 37, line 1058—Saves data pointer before commencement of subroutine.

Page 37, lines 1060-1061—Set up auto-indexing through operator-selected zoning limits.

Page 37, lines 1065-1067—Data is brought into accumulator.

Page 37, lines 1068—Adjustment made for small defects.

Page 37, lines 1065-1071—Compares actual XD1 data with zoning limits.

Page 37, line 1074—Is there a defect in Zone A?

Page 37, lines 1077-1085—Compares actual XD2 data with zoning limits.

Page 38, lines 1088-1094—Compares actual MD1 data with zoning limits.

Page 38, lines 1097-1102—Compares actual MD2 data with zoning limits.

Page 38, lines 1105-1110—Compares actual STRK XD1 data with zoning limits.

Page 38, lines 1113-1117—Compares actual STRK XD2 data with zoning limits.

Page 38, line 1120—End of defect zoning task.

Pages 39 et seq.—These appendices are not computational software but, instead, are aids to software programmers; they contain symbol and cross-reference tables.

/PARAMETERS FOR P Q I (V2B-A)     PAL8-V10A 02/02/77  PAGE 1

| | | | | |
|---|---|---|---|---|
| 1 | | | /PARAMETERS FOR P Q I (V2B-A) | |
| 2 | | | | |
| 3 | | | /TASK TABLE SETUP - "TASK", "CUR","INIWT", AND "START" | |
| 4 | | | /MUST BE DEFINED BY TASK: | |
| 5 | | | | |
| 6 | | | | |
| 7 | | 1422 | *TASK^2+MSGTBL | |
| 8 | 01422 | 0000 | ZBLOCK 2 | /MESSAGE BUFFER INITIALLY CLEAR |
| 9 | | 1544 | *TASK^4+TSTABL | |
| 10 | 01544 | 0011 | CUR%10+CUR | /INITIAL FLAGS |
| 11 | 01545 | 3600 | START | |
| 12 | 01546 | 0000 | 0 | /INITIAL AC 0 |
| 13 | 01547 | 0001 | VERS | /INITIAL MQ |
| 14 | | 1711 | *TASK+TFTABL | |
| 15 | 01711 | 0000 | INIWT | |
| 16 | | | | |
| 17 | | 1430 | *TASK2^2+MSGTBL | |
| 18 | 01430 | 0000 | ZBLOCK 2 | /MESSAGE BUFFER INITIALLY CLEAR |
| 19 | | 1560 | *TASK2^4+TSTABL | |
| 20 | 01560 | 0011 | CUR2%10+CUR2 | /INITIAL FLAGS2 |
| 21 | 01561 | 4400 | START2 | |
| 22 | 01562 | 0000 | 0 | /INITIAL AC 0 |
| 23 | 01563 | 0001 | VERS2 | /INITIAL MQ |
| 24 | | 1714 | *TASK2+TFTABL | |
| 25 | 01714 | 0000 | INIWT2 | |
| 26 | | | | |
| 27 | | 1426 | *TASK3^2+MSGTBL | |
| 28 | 01426 | 0000 | ZBLOCK 2 | /MESSAGE BUFFER INITIALLY CLEAR |
| 29 | | 1554 | *TASK3^4+TSTABL | |
| 30 | 01554 | 0011 | CUR3%10+CUR3 | /INITIAL FLAGS3 |
| 31 | 01555 | 4600 | START3 | |
| 32 | 01556 | 0000 | 0 | /INITIAL AC 0 |
| 33 | 01557 | 0001 | VERS3 | /INITIAL MQ |
| 34 | | 1713 | *TASK3+TFTABL | |
| 35 | 01713 | 0000 | INIWT3 | |

/ QUALITY SCREENING AND ZONING     PAL8-V10A 02/02/77  PAGE 14

| | | | |
|---|---|---|---|
| 36 | | / QUALITY SCREENING AND ZONING | 2/2/77 |
| 37 | | | |
| 38 | 0001 | VERS=1 | |
| 39 | 0001 | VERS2=1 | |
| 40 | 0001 | VERS3=1 | |

```
41                      /
42                      /
43                      /%RS     PRODUCT QUALITY DECISION TASKS
44                      /
45                      /%TW     THIS GROUP OF TASKS LOOKS AT THE DATA FOR A
46                      /        WHOLE SHEET (ALL THREE CHANNELS) AND MAKES
47                      /        AN INITIAL DECISION AS TO THE QUALITY OF THE
48                      /        SHEET. THE ZONING TASK IS INCLUDED HERE.
49                      /
50                      /
51             0012             TASK=    QUAL               /BASIC SHEET PROCESSING
52             0010             CUR=     QUALFLD
53             0000             INIWT=   0                  /INITIALLY RUNNABLE.
54
55             0015             TASK2=   QFIN               /FINAL SHEET BOOKKEEPING
56             0010             CUR2=    CUR
57             0000             INIWT2=  0
58
59             0014             TASK3=   ZONE               /ZONING ALGORITHM
60             0010             CUR3=    CUR2
61             0000             INIWT3=  0
62
63             0001             FIELD CUR%10
64
65             0130             *QUALPGZ
66
67    10130    0000     SHSTAT, 0                           /COMBINED INSPECTOR STATUS WORD FOR
68                                                          /THIS SHEET.
69    10131    0000     QUSCR,  0                           /QUAL SCRATCH LOCATION.
70    10132    0014     PFADJ,  14                          /SMALL DEFECT PICTURE FRAME OFFSET.
71    10133    2130     CH2SCF, 2130                        /CHANNEL 2 SCALE FACTOR, CURRENTLY
72                                                          / = 1112 DECIMAL.
73    10134    0010     CH2ADJ, 10                          /DATA SHIFT FOR THE INSPECTOR MASK.
74
75
76             3600             *QUALLOC

/ QUALITY SCREENING AND ZONING               PAL8-V10A 02/02/77   PAGE 15

77                      /
78                      /
79                      /        DEFINITION OF THE FEATURE ADDRESS LABELS -
80                      /
81                      /
82                      /
83                      /FEATURE  RELATIVE           FEATURE
84                      / LABEL   ADDRESS            DESCRIPTION
85
86
87             0000     PSDXD=    00                 /PEAK SMALL DEFECT XD LOCATION
88             0001     PSDMD=    01                 /PEAK SMALL DEFECT MD LOCATION
89             0002     PLDXDP=   02                 /PEAK POSTIVE LARGE DEFECT XD LOC.
90             0003     PLDMDP=   03                 /PEAK POSITIVE LARGE DEFECT MD LOC.
91             0004     PLDXDN=   04                 /PEAK NEGATIVE LARGE DEFECT XD LOC.
92             0005     PLDMDN=   05                 /PEAK NEGATIVE LARGE DEFECT MD LOC.
93             0006     XD1=      06                 /DEFECT STARTING LOCATION - XD
94             0007     XD2=      07                 /DEFECT ENDING LOCATION - XD
95
96             0010     MD1=      10                 /DEFECT STARTING LOCATION - MD
97             0011     MD2=      11                 /DEFECT ENDING LOCATION - MD
98             0012     ISTATUS=  12       /*        /INSPECTOR DEFECT STATUS WORD
99             0013     NUMDEF=   13                 /NUMBER OF DEFECTS IN MD
100            0014     STK1=     14                 /STREAK STARTING LOCATION - XD
101            0015     EMULFT=   15                 /EMULSION FAULT REFERENCE
102            0016     TOTPA=    16       /*        /TOTAL POSITIVE DEFECTIVE AREA (LSB)
103            0017     MSBW1=    17       /*        /MSB'S OF "TOTPA" & "PIAT"
104
105            0020     TOTNA=    20       /*        /TOTAL NEGATIVE DEFECTIVE AREA (LSB)
106            0021     MSBW2=    21       /*        /MSB'S OF "TOTNA" & "NIAT"
107            0022     SDAUTO=   22                 /SMALL DEFECT AUTOCAL
108            0023     PIAT=     23       /*        /POSITIVE IAT (LSB)
109            0024     NIAT=     24       /*        /NEGATIVE IAT (LSB)
110            0025     SDPK=     25                 /SMALL DEFECT PEAK AMPLITUDE
111            0026     LDPKP=    26                 /POSITIVE LARGE DEFECT PEAK AMPL.
```

```
112     0027    LDPKN=      27      /NEGATIVE LARGE DEFECT PEAK AMPL.
113
114     0030    STK2=       30      /STREAK ENDING LOCATION - XD
115     0031    XDMAX=      31      /MAXIMUM XD DURATION
116     0032    MDMAX=      32      /MAXIMUM MD DURATION
117     0033    STPKP=      33      /POSITIVE STREAK PEAK AMPLITUDE
118     0034    STPKN=      34      /NEGATIVE STREAK PEAK AMPLITUDE
119     0035    EFPKP=      35      /POSITIVE EMULSION FAULT PEAK AMPL.
120     0036    EFPKN=      36      /NEGATIVE EMULSION FAULT PEAK AMPL.
121     0037    CHECKW=     37      /CHECK WORD TERMINATOR (7777)
122             /
123             /
124             /
125             /       /*  SEE DATA FORMAT DETAILS ON THE NEXT PAGE.
126             /
127             /

/ QUALITY SCREENING AND ZONING           PAL8-V10A 02/02/77  PAGE 16

128             /
129             /
130             /
131             /       DATA FORMAT DETAILS FOR PACKED DATA WORDS
132             /
133             /
134             /   FEATURE          DATA DESCRIPTION
135             /   LABEL
136             /
137             /
138             /   ISTATUS      BIT 0-4 NOT USED (ZERO)
139             /                    5   ROLL MARK
140             /                    6   STREAK
141             /                    7   SMALL DEFECT
142             /                    8   LARGE DEFECT
143             /                    9   EMULSION FAULT
144             /                   10   SPLICE
145             /                   11   EDGE DEFECT
146             /
147             /
148             /   TOTPA        THE 12 LSB'S OF THE TOTAL POSITIVE
149             /                DEFECTIVE AREA.
150             /
151             /
152             /   MSBW1        BIT 0-4    NOT USED (ZERO)
153             /                    5-8    MSB'S OF THE "PIAT"
154             /                    9-11   MSB'S OF THE "TOTPA"
155             /
156             /
157             /   TOTNA        THE 12 LSB'S OF THE TOTAL NEGATIVE
158             /                DEFECTIVE AREA.
159             /
160             /
161             /   MSBW2        BIT 0-4    NOT USED (ZERO)
162             /                    5-8    MSB'S OF THE "NIAT"
163             /                    9-11   MSB'S OF THE "TOTNA"
164             /
165             /
166             /   PIAT         THE 12 LSB'S OF THE POSITIVE INTEGRATE
167             /                ABOVE A THRESHOLD VALUE.
168             /
169             /
170             /   NIAT         THE 12 LSB'S OF THE NEGATIVE INTEGRATE
171             /                ABOVE A THRESHOLD VALUE.
172             /
173             /

/ QUALITY SCREENING AND ZONING           PAL8-V10A 02/02/77  PAGE 17

174             /
175             /
176             /XRT     QUAL - ANALYZE THE QUALITY OF A SHEET
177             /
178             /XTW     THIS TASK CONTROLS THE DETERMINATION OF SHEET
```

```
179             /       QUALITY, IT IS RUN BY "CH3" AFTER THE CHANNEL 3
180             /       DATA FOR THIS SHEET IS IN THE DATA BUFFER, AFTER
181             /       VERIFYING THE SHEET DATA FROM ALL 3 INSPECTOR
182             /       CHANNELS HAS BEEN RECEIVED, AND SCALING THE
183             /       CHANNEL 2 MACHINE DIRECTION DEPENDENT (XD) DATA,
184             /       THE INITIAL SHEET QUALITY IS DETERMINED, THEN A
185             /       QUALITY MESSSAGE IS QUEUED FOR MEMORY.
186             /
187             /%TW    THE SHEET QUALITY MESSAGES SENT TO MEMORY DEPEND
188             /       ON THE MODE IN WHICH #12 IS RUN. WHEN #12 IS ZONING
189             /       ALL MESSAGE TYPES ARE USED AS DESCRIBED BELOW.
190             /       HOWEVER, WHEN #12 IS NOT ZONING, THE "NO DATA"
191             /       MESSAGE IS SENT FOR EACH SHEET, EXCEPT WHEN PQI
192             /       WANTS TO OVERRIDE THE DEFECT DATA THAT MEMORY HAS
193             /       RECEIVED FROM THE INSPECTOR. THIS IS USED WHEN THE
194             /       DEFECT IS FOUND TO BE IN THE PICTURE FRAME AREA.
195             /
196             /%TW    DURING ZONING, THE FOLLOWING MESSAGES ARE USED:
197             /       IF THE DATA FROM 1 OR MORE INSPECTOR CHANNELS IS
198             /       MISSING, A "NO DATA" MESSAGE IS SENT TO MEMORY. IF
199             /       ALL 3 INSPECTOR CHANNELS SAY NO DEFECTS, A "GOOD
200             /       SHEET" IS SENT. IF THE INSPECTOR SAW A HARD DEFECT
201             /       (EDGE DEFECT, SPLICE, OR EMULSION FAULT), A "REJECT
202             /       SHEET" MESSAGE IS USED. IF THE DEFECT IS IN THE
203             /       SOFT CLASS (LARGE DEFECT, SMALL DEFECT, STREAK, OR
204             /       ROLL MARK), "QUAL" CHECKS IF THE DEFECT IS IN THE
205             /       PICTURE FRAME, AND IF IT IS, SENDS MEMORY A "GOOD
206             /       SHEET" MESSAGE. IF THE DEFECT IS NOT IN THE PICTURE
207             /       FRAME AREA, CONTROL RETURNS TO
208             /       "QFIN" WHICH QUEUES THE SHEET QUALITY
209             /       MESSAGE TO MEMORY. THE SHEET QUALITY IS ALSO PUT
210             /       IN THE HIGH-ORDER BITS OF WORD 17 IN THE CHANNEL 1
211             /       DATA FOR THIS SHEET.

/ QUALITY SCREENING AND ZONING                PAL8-V10A  02/02/77   PAGE 18

212             /
213             /
214             /       ANALYZE THE QUALITY OF A SHEET.
215             /
216             /
217  13600 7300 START,  CLB
218  13601 4020         CAL
219  13602 0004         SUSPND          /GO TO SLEEP TIL THE NEXT SHEET.
220             /
221             /
222             /       SEND THE LAST SHEET QUALITY MESSAGE TO MEMORY
223             /
224             /
225  13603 7330         AC4000          /SET BIT 0 - FOR LHN TIMING.
226  13604 6516         DBSO DR851
227  13605 7300         CLB
228  13606 1053         TAD SHDONE      /ADD THE SHEET DECISION ACTIVE FLAG
229  13607 1777'        TAD QUMG1       /TO THE EVENT FLAG FOR THE QUALITY
230                                     /MESSAGE TO MEMORY.
231  13610 7650         SNA CLA         /ARE THEY BOTH FINISHED ?
232  13611 5224         JMP QUAL1       /ALL DONE, GO ON TO THIS SHEET.
233  13612 3053         DCA SHDONE      /CLEAR THE SHEET ACTIVE FLAG NOW TO
234                                     /AVOID AN ENDLESS LOOP.
235  13613 1776'        TAD QUERMG      /IS THE ERROR ALREADY TYPING ?
236  13614 7640         SZA CLA
237  13615 5222         JMP .+5         /YES, ONLY DO ONE AT A TIME.
238  13616 4020         CAL
239  13617 0000         SEND
240  13620 0025         TTYS            /LOG "OVERSPEED ERROR"
241  13621 4323         QUERMG
242  13622 7300         CLB
243  13623 3066         DCA LASTQL      /CLEAR THE DATA MESSAGE TO TELL
244                                     /MEMORY "NO DATA".
245
246  13624 1066 QUAL1,  TAD LASTQL      /GET THE QUALITY CODE FOR THE LAST
247  13625 7450         SNA             /SHEET. IS IT ZERO ?
248  13626 1375         TAD (1000)      /YES, FORCE "NO DATA" MESSAGE.
249  13627 3774'        DCA QUMG1+3     /PUT IT IN THE MESSAGE TO MEMORY.
```

| | | | | | |
|---|---|---|---|---|---|
| 250 | 13630 | 3066 | | DCA LASTQL | /CLEAR THE MESSAGE STORAGE WORD. |
| 251 | 13631 | 4020 | | CAL | /QUEUE THE MESSAGE FOR MEMORY. |
| 252 | 13632 | 0000 | | SEND | |
| 253 | 13633 | 0007 | | TALK | |
| 254 | 13634 | 4341 | | QUMG1 | |
| 255 | | | | | |
| 256 | 13635 | 7301 | | CLB IAC | /SET THE SHEET DECISION ACTIVE FLAG. |
| 257 | 13636 | 3053 | | DCA SHDONE | |

/ QUALITY SCREENING AND ZONING    PAL8-V10A 02/02/77  PAGE 19

| | | | | | |
|---|---|---|---|---|---|
| 258 | | | / | | |
| 259 | | | / | | |
| 260 | | | / | COMPUTE THE LOCATION OF THE DATA FOR THE | |
| 261 | | | / | THREE CHANNELS IN THE SHEET DATA BUFFER. | |
| 262 | | | / | | |
| 263 | | | / | | |
| 264 | 13637 | 1041 | | TAD CH3LOC | /COMPUTE THE BASE ADDRESS OF THE |
| 265 | 13640 | 1373 | | TAD (-40) | /CHANNEL 1 DATA FOR THIS SHEET. |
| 266 | 13641 | 0372 | | AND (3777) | |
| 267 | 13642 | 1371 | | TAD (DATBAS) | |
| 268 | 13643 | 3063 | | DCA CH1BAS | /SAVE FOR LATER USE. |
| 269 | 13644 | 1041 | | TAD CH3LOC | /NOW DO THE SAME FOR CHANNEL 2. |
| 270 | 13645 | 1370 | | TAD (-100) | |
| 271 | 13646 | 0372 | | AND (3777) | |
| 272 | 13647 | 1371 | | TAD (DATBAS) | |
| 273 | 13650 | 3064 | | DCA CH2BAS | |
| 274 | 13651 | 1041 | | TAD CH3LOC | /AND LASTLY CHANNEL 3. |
| 275 | 13652 | 1367 | | TAD (-140) | /BACK UP 1 SHEET. |
| 276 | 13653 | 0372 | | AND (3777) | |
| 277 | 13654 | 1371 | | TAD (DATBAS) | |
| 278 | 13655 | 3065 | | DCA CH3BAS | |
| 279 | | | / | | |
| 280 | | | / | | |
| 281 | | | / | CHECK FOR VALID DATA FROM ALL THREE CHANNELS. | |
| 282 | | | / | EACH DATA SET MUST HAVE THE TERMINATOR (7777). | |
| 283 | | | / | | |
| 284 | | | / | | |
| 285 | 13656 | 1063 | | TAD CH1BAS | /LOOK FOR THE -1 DATA TERMINATOR. |
| 286 | 13657 | 4766' | | JMS GETDAT | /IT WILL BE THERE IF THE DATA IS |
| 287 | 13660 | 0037 | | CHECKW | /COMPLETE. |
| 288 | 13661 | 7001 | | IAC | |
| 289 | 13662 | 7640 | | SZA CLA | |
| 290 | 13663 | 5300 | | JMP QUAL2 | /GO TELL MEMORY - NO DECISION. |
| 291 | 13664 | 1064 | | TAD CH2BAS | /NOW CHECK CHANNEL 2. |
| 292 | 13665 | 4766' | | JMS GETDAT | |
| 293 | 13666 | 0037 | | CHECKW | |
| 294 | 13667 | 7001 | | IAC | |
| 295 | 13670 | 7640 | | SZA CLA | |
| 296 | 13671 | 5300 | | JMP QUAL2 | /NO DATA, GO TELL MEMORY. |
| 297 | 13672 | 1065 | | TAD CH3BAS | /AND LASTLY CHECK CHANNEL 3. |
| 298 | 13673 | 4766' | | JMS GETDAT | |
| 299 | 13674 | 0037 | | CHECKW | |
| 300 | 13675 | 7001 | | IAC | |
| 301 | 13676 | 7650 | | SNA CLA | |
| 302 | 13677 | 5302 | | JMP QUAL3 | /DATA OK, GO ON. |
| 303 | 13700 | 1375 | QUAL2, | TAD (1000) | /SET UP THE "NO DATA" MESSAGE AND |
| 304 | 13701 | 5765' | | JMP QUAL7 | /EXIT. |

/ QUALITY SCREENING AND ZONING    PAL8-V10A 02/02/77  PAGE 20

| | | | | | |
|---|---|---|---|---|---|
| 305 | | | / | | |
| 306 | | | / | | |
| 307 | | | / | COLLECT AND "OR" THE THREE DEFECT STATUS WORDS | |
| 308 | | | / | | |
| 309 | | | / | | |
| 310 | 13702 | 1063 | QUAL3, | TAD CH1BAS | /GET THE INSPECTOR STATUS WORD FOR |
| 311 | 13703 | 4766' | | JMS GETDAT | /CHANNEL 1 |
| 312 | 13704 | 0012 | | ISTATUS | |
| 313 | 13705 | 7421 | | MQL | /SAVE IT IN THE MQ. |
| 314 | 13706 | 1064 | | TAD CH2BAS | /GET THE CHANNEL 2 STATUS WORD. |
| 315 | 13707 | 4766' | | JMS GETDAT | |

| | | | | | |
|---|---|---|---|---|---|
| 316 | 13710 | 0012 | | ISTATUS | |
| 317 | 13711 | 7501 | | MQA | /"OR" WITH CHANNEL 1 |
| 318 | 13712 | 7421 | | MQL | /AND SAVE AGAIN. |
| 319 | 13713 | 1065 | | TAD CH3BAS | /AND NOW DO CHANNEL 3. |
| 320 | 13714 | 4766' | | JMS GETDAT | |
| 321 | 13715 | 0012 | | ISTATUS | |
| 322 | 13716 | 7501 | | MQA | /ALL 3 STATUS WORDS OR'ED. |
| 323 | 13717 | 3130 | | DCA SHSTAT | /SAVE THE COMBINED SHEET STATUS. |
| 324 | | | / | | |
| 325 | | | / | | |
| 326 | | | / | ADJUST CHANNEL 2 DATA FOR "XD" AND "STR" SINCE THAT | |
| 327 | | | / | CHANNEL IS MASKED IN THE INSPECTOR. CHANNEL 2 ALSO | |
| 328 | | | / | HAS A LONGER LASER BEAM PATH LENGTH AND NEEDS TO BE | |
| 329 | | | / | SCALED TO AGREE WITH THE DATA FOR CHANNELS 1 AND 2. | |
| 330 | | | / | THIS ADJUSTMENT IS NEEDED TO EVALUATE THE "PICTURE | |
| 331 | | | / | FRAME" AND FOR PROPER ZONING. THE SCALE EQUATION | |
| 332 | | | / | IS OF THE FORM: CH2(I) = A*CH2(I) + B. | |
| 333 | | | / | | |
| 334 | | | / | | |
| 335 | 13720 | 7431 | QUAL4, | SWAB | /ENSURE EAE MODE "B". |
| 336 | 13721 | 1064 | | TAD CH2BAS | /GET THE DATA BASE ADDRESS FOR |
| 337 | 13722 | 4766' | | JMS GETDAT | /CHANNEL 2 AND GO GET THE "XD1" |
| 338 | 13723 | 0006 | | XD1 | /DATA WORD. |
| 339 | 13724 | 7104 | | CLL RAL | /CHECK IF DATA = 3777, WHICH IS OFF- |
| 340 | 13725 | 7510 | | SPA | /SHEET AND MEANS NO DEFECT. |
| 341 | 13726 | 5764' | | JMP QUAL4A | /IT IS 3777, DO NOT SCALE. |
| 342 | 13727 | 7110 | | CLL RAR | /RESTORE DATA AFTER TEST. |
| 343 | 13730 | 7421 | | MQL | /NOW SCALE DATA BY FIRST MULTIPLING |
| 344 | 13731 | 7405 | | MUY | /BY 1XXX AND THEN DIVIDING BY 1000. |
| 345 | 13732 | 0133 | | CH2SCF | |
| 346 | 13733 | 7407 | | DVI | /THIS HAS THE EFFECT OF MULTIPLING |
| 347 | 13734 | 3763 | | (1750) | /THE DATA BY 1.XXX, WHICH IS NOT |
| 348 | 13735 | 7701 | | ACL | /POSSIBLE WITH INTEGER ARITHMATIC. |
| 349 | 13736 | 1134 | | TAD CH2ADJ | /ADD IN THE INSPECTOR MASK OFFSET. |
| 350 | 13737 | 4762' | | JMS PUTDAT | /"XD1" IS NOW FUDGED, PUT IT BACK. |
| 351 | 13740 | 5764' | | JMP QUAL4A | |

/ QUALITY SCREENING AND ZONING          PAL8-V10A 02/02/77  PAGE 21

| | | | | | |
|---|---|---|---|---|---|
| 352 | | | / | | |
| 353 | | | | | |
| 354 | | | | | |
| 355 | 13762 | 4244 | | | |
| 356 | 13763 | 1750 | | | |
| 357 | 13764 | 4000 | | | |
| 358 | 13765 | 4226 | | | |
| 359 | 13766 | 4234 | | | |
| 360 | 13767 | 7640 | | | |
| 361 | 13770 | 7700 | | | |
| 362 | 13771 | 2000 | | | |
| 363 | 13772 | 3777 | | | |
| 364 | 13773 | 7740 | | | |
| 365 | 13774 | 4344 | | | |
| 366 | 13775 | 1000 | | | |
| 367 | 13776 | 4323 | | | |
| 368 | 13777 | 4341 | | | |
| 369 | | 4000' | | PAGE | |

/ QUALITY SCREENING AND ZONING          PAL8-V10A 02/02/77  PAGE 22

| | | | | | |
|---|---|---|---|---|---|
| 370 | | | / | | |
| 371 | | | / | | |
| 372 | | | / | | |
| 373 | | | / | CONTINUE CHANNEL 2 DATA SCALING | |
| 374 | | | / | | |
| 375 | | | / | | |
| 376 | 14000 | 7300 | QUAL4A, | CLB | |
| 377 | 14001 | 1064 | | TAD CH2BAS | /DO THE SAME FOR "XD2". |
| 378 | 14002 | 4777' | | JMS GETDAT | |
| 379 | 14003 | 0007 | | XD2 | |
| 380 | 14004 | 7450 | | SNA | /IF THE DATA IS ZERO, LEAVE IT ZERO. |
| 381 | 14005 | 5216 | | JMP QUAL4B | /WAS ZERO, OFF-SHEET, NO DEFECT. |
| 382 | 14006 | 7421 | | MQL | |
| 383 | 14007 | 7405 | | MUY | /SCALE DATA AS ABOVE. |

```
384  14010  0133         CH2SCF
385  14011  7407         DVI
386  14012  4176         (1750)
387  14013  7701         ACL
388  14014  1134         TAD CH2ADJ    /OFFSET IT FOR THE MASK AND
389  14015  4775'        JMS PUTDAT    /PUT IT BACK IN THE DATA BUFFER.
390
391  14016  1064  QUAL4B, TAD CH2BAS   /NOW DO "STK1".
392  14017  4777'        JMS GETDAT
393  14020  0014         STK1
394  14021  7104         CLL RAL       /DO OFF-SHEET TEST AS PER XD1.
395  14022  7510         SPA
396  14023  5235         JMP QUAL4C    /OFF-SHEET, GO ON.
397  14024  7110         CLL RAR
398  14025  7421         MQL
399  14026  7405         MUY           /SCALE AS ABOVE.
400  14027  0133         CH2SCF
401  14030  7407         DVI
402  14031  4176         (1750)
403  14032  7701         ACL
404  14033  1134         TAD CH2ADJ
405  14034  4775'        JMS PUTDAT
406
407  14035  7300  QUAL4C, CLB
408  14036  1064         TAD CH2BAS    /AND FINALLY FUDGE "STK2".
409  14037  4777'        JMS GETDAT
410  14040  0030         STK2
411  14041  7450         SNA           /(SAME TREATMENT AS "XD2".)
412  14042  5253         JMP QUAL4D    /OFF-SHEET, GO ON.
413  14043  7421         MQL
414  14044  7405         MUY           /SCALE AS ABOVE.
415  14045  0133         CH2SCF
416  14046  7407         DVI
417  14047  4176         (1750)
418  14050  7701         ACL
419  14051  1134         TAD CH2ADJ
420  14052  4775'        JMS PUTDAT

/ QUALITY SCREENING AND ZONING       PAL8-V10A  02/02/77   PAGE 23

421          /
422          /
423          /
424          /       AND STILL MORE CHANNEL 2 DATA SCALING
425          /
426          /
427  14053  1064  QUAL4D, TAD CH2BAS   /WHILE WE'RE AT IT WE MIGHT AS WELL
428  14054  4777'        JMS GETDAT    /ADJUST THE OTHER XD TYPE VALUES.
429  14055  0000         PSDXD
430  14056  7421         MQL
431  14057  7405         MUY           /SCALE AS ABOVE FOR "XD" AND "STK".
432  14060  0133         CH2SCF
433  14061  7100         CLL           /CLEAR THE LINK FOR OVERFLOW TEST.
434  14062  7407         DVI
435  14063  4176         (1750)
436  14064  7630         SZL CLA       /DIVIDE OVERFLOW ?  CAN HAPPEN HERE
437                                    /IF THE DATA WAS ZERO.
438  14065  5271         JMP .+4       /YES, DON'T PUT IT BACK.
439  14066  7701         ACL
440  14067  1134         TAD CH2ADJ    /ADD IN THE MASK OFFSET, AND
441  14070  4775'        JMS PUTDAT    /PUT THE DATA BACK IN THE BUFFER.
442  14071  1064         TAD CH2BAS
443  14072  4777'        JMS GETDAT
444  14073  0002         PLDXDP
445  14074  7421         MQL
446  14075  7405         MUY           /SCALE AS ABOVE
447  14076  0133         CH2SCF
448  14077  7100         CLL
449  14100  7407         DVI
450  14101  4176         (1750)
451  14102  7630         SZL CLA
452  14103  5307         JMP .+4
453  14104  7701         ACL
454  14105  1134         TAD CH2ADJ
455  14106  4775'        JMS PUTDAT
```

```
456
457   14107   1064            TAD CH2BAS
458   14110   4777'           JMS GETDAT
459   14111   6004            PLDXDN
460   14112   7421            MQL
461   14113   7405            MUY             /SAME AS ABOVE.
462   14114   0133            CH2SCF
463   14115   7100            CLL
464   14116   7407            DVI
465   14117   4176            (1750)
466   14120   7630            SZL CLA
467   14121   5325            JMP .+4
468   14122   7701            ACL
469   14123   1134            TAD CH2ADJ
470   14124   4775'           JMS PUTDAT      /SCALING ALL DONE.
```

/ QUALITY SCREENING AND ZONING            PAL8-V10A 02/02/77  PAGE 24

```
471                   /
472                   /
473                   /
474                   /       EVALUATE THE SHEET DEFECT STATUS
475                   /
476                   /
477   14125   7300            CLB
478
479   14126   7410            SKP             /DO THE FOLLOWING TEST FOR NOW
480
481   14127   7000            NOP
482
483
484   14130   1130            TAD SHSTAT      /WAS THERE A DEFECT ON THIS SHEET ?
485   14131   7640            SZA CLA
486   14132   5774'           JMP QUAL5       /YES, GO PROCESS THE FEATURE DATA.
487   14133   1373            TAD (1000)      /NO, SET UP TO SAY "NO INFO" AND
488   14134   5772'           JMP QUAL7       /EXIT.
489
490   14172   4226
491   14173   1000
492   14174   4200
493   14175   4244
494   14176   1750
495   14177   4234
496           4200'           PAGE
```

/ QUALITY SCREENING AND ZONING            PAL8-V10A 02/02/77  PAGE 25

```
497                   /
498                   /
499                   /
500                   /       CHECK IF WE HAVE  O N L Y  SMALL DEFECTS
501                   /       IN THE PICTURE FRAME AREA.
502                   /
503                   /
504   14200   7300    QUAL5,  CLB
505   14201   5221            JMP QUAL6       /NOP PICTURE FRAME FOR NOW
506
507   14202   1130            TAD SHSTAT      /DOES THIS SHEET CONTAIN ONLY SMALL
508   14203   0377            AND (7757)      /DEFECTS ?
509   14204   7640            SZA CLA
510   14205   5221            JMP QUAL6       /NO, GO ON, NO PICTURE FRAMING.
511
512   14206   1063            TAD CH1BAS      /YES, FIRST LOOK AT CHANNEL 1 DATA.
513   14207   4252            JMS QUALS1
514   14210   5221            JMP QUAL6       /DEFECTS OUTSIDE THE PICTURE FRAME.
515   14211   1064            TAD CH2BAS      /NOW LOOK AT CHANNEL 2.
516   14212   4252            JMS QUALS1
517   14213   5221            JMP QUAL6
518   14214   1065            TAD CH3BAS      /AND AT LAST CHANNEL 3.
519   14215   4252            JMS QUALS1
520   14216   5221            JMP QUAL6
521   14217   1376            TAD (7001)      /THE DEFECTS WERE ONLY INSIDE THE
522   14220   5226            JMP QUAL7       /"PICTURE FRAME", SAY "GOOD SHEET".
```

```
523                   /
524                   /
525                   /      THE DEFECTS ARE NOT IN THE PICTURE FRAME, RUN
526                   /      THE "PQA" TASK TO DETERMINE SHEET QUALITY.
527                   /
528                   /
529   14221  7300  QUAL6,  CLB
530   14222  1375          TAD (ZONE)     /RUN "ZONE" TO CKECK FOR ZONING
531   14223  4020          CAL
532   14224  0003          RUN
533   14225  5774!         JMP START      /BACK TO SLEEPY-VILLE.
534                   /
535                   /
536                   /      SAVE THE VALUE FOR THIS SHEET AND EXIT.
537                   /
538                   /
539   14226  3066  QUAL7,  DCA LASTQL     /SAVE THE MESSAGE FOR MEMORY.
540
541   14227  1373          TAD (QFIN)     /NOW WE CAN RUN THE "FINISH" TASK T
542   14230  4020          CAL            /COMPLETE THE PROCESSING OF THIS
543   14231  0003          RUN            /SHEET.
544   14232  5774!         JMP START      /NOW GO BACK TO SLEEP.

/ QUALITY SCREENING AND ZONING              PAL8-V10A 02/02/77  PAGE 26

545                   /
546                   /
547                   /
548                   /      SUBROUTINE TO GET A WORD OF DATA OUT OF THE
549                   /      SHEET DATA TABLE. THE BASE ADDRESS IS IN THE
550                   /      ACCUMULATOR WHEN CALLED, AND THE DATA OFFSET
551                   /      FOLLOWS THE CALL. THE DATA FROM THE DESIRED
552                   /      LOCATION IS RETURNED IN THE ACCUMULATOR.
553                   /
554                   /
555   14233  0000          0
556   14234  0000  GETDAT, 0
557   14235  1634          TAD I GETDAT   /ADD IN THE OFFSET.
558   14236  2234          ISZ GETDAT
559   14237  3233          DCA GETDAT-1   /SAVE FOR INDIRECT ADDRESS.
560   14240  6221          CDF DATFLD     /SET THE DATA FIELD TO THE BUFFER.
561   14241  1633          TAD I GETDAT-1 /GET THE DESIRED DATA WORD.
562   14242  6211          CDF CUR        /RESET THE DATA FIELD TO HERE.
563   14243  5634          JMP I GETDAT   /RETURN.
564                   /
565                   /
566                   /      SUBROUTINE TO PUT DATA BACK IN THE SHEET DATA
567                   /      TABLE AT THE ADDRESS LEFT BY "GETDAT". "GETDAT"
568                   /      COMPUTES THE DATA ADDRESS FOR "PUTDAT".
569                   /
570                   /
571   14244  0000  PUTDAT, 0
572   14245  6221          CDF DATFLD     /SET THE DATA FIELD TO THE BUFFER.
573   14246  3633          DCA I GETDAT-1 /PUT THE DATA BACK IN THE BUFFER.
574   14247  6211          CDF CUR        /RESET THE DATA FIELD TO HERE.
575   14250  7300          CLB
576   14251  5644          JMP I PUTDAT   /RETURN.

/ QUALITY SCREENING AND ZONING              PAL8-V10A 02/02/77  PAGE 27

577                   /
578                   /
579                   /      SUBROUTINE TO LOOK FOR DEFECTS THAT ARE WITHIN
580                   /      THE "PICTURE FRAME" ONLY. IF A DEFECT IS FOUND
581                   /      OUTSIDE THE "PICTURE FRAME", EXIT IMMEDIATELY:
582                   /      THERE IS NO POINT IN LOOKING FURTHER.
583                   /
584                   /
585   14252  0000  QUALS1, 0
586   14253  3322          DCA QUAPTR     /SAVE THE CHANNEL DATA POINTER.
587
```

```
588   14254   1322            TAD QUAPTR       /GET THE XD1 DATA FOR THIS CHANNEL.
589   14255   4234            JMS GETDAT
590   14256   0006            XD1
591   14257   1316            TAD PFXD1
592   14260   7700            SMA CLA
593   14261   5270            JMP QUALSA       /XD IS OK, LOOK AT MDMAX.
594
595   14262   1322            TAD QUAPTR       /GET THE XD2 DATA.
596   14263   4234            JMS GETDAT
597   14264   0007            XD2
598   14265   1317            TAD PFXD2
599   14266   7740            SMA SZA CLA
600   14267   5277            JMP QUALSB       /OUTSIDE THE XD PICTURE FRAME, GO O
601
602   14270   1322    QUALSA, TAD QUAPTR       /CHECK THAT THE DEFECT IS LESS THAN
603   14271   4234            JMS GETDAT       /10(10) SCANS LONG.
604   14272   0032            MDMAX
605   14273   1372            TAD (-12)
606   14274   7750            SPA SNA CLA      /SKIP IF THE DEFECT IS TOO LONG.
607   14275   2252            ISZ QUALS1       /INCREMENT THE RETURN ADDRESS TO SA
608                                            /THIS CHANNEL EITHER CONTAINS NO
609                                            /DEFECT OR THE DEFECT IS IN THE XD
610                                            /PICTURE FRAME.
611   14276   5652            JMP I QUALS1     /RETURN.
612
613   14277   5652    QUALSB, JMP I QUALS1     /SERVES AS A NOP FOR NOW !!
614   14300   1322            TAD QUAPTR       /CHECK THE MD PICTURE FRAME AREA.
615   14301   4234            JMS GETDAT
616   14302   0010            MD1
617   14303   1320            TAD PFMD1
618   14304   7700            SMA CLA
619   14305   5314            JMP QUALSC       /MD IS OK, GO ON.
620
621   14306   1322            TAD QUAPTR       /NOW CHECK MD2
622   14307   4234            JMS GETDAT
623   14310   0011            MD2
624   14311   1321            TAD PFMD2
625   14312   7740            SMA SZA CLA
626   14313   5652            JMP I QUALS1     /OUTSIDE THE MD PICTURE FRAME, EXIT.
627
628   14314   2252    QUALSC, ISZ QUALS1       /INCREMENT THE RETURN ADDRESS TO SA
629   14315   5652            JMP I QUALS1     /THIS CHANNEL EITHER CONTAINS NO
630                                            /DEFECTS OR THE DEFECT IS IN THE
631                                            /PICTURE FRAME.

/ QUALITY SCREENING AND ZONING           PAL8-V10A 02/02/77  PAGE 28

632                   /
633                   /
634                   /
635                   /       PICTURE FRAME BOUNDARIES
636                   /
637                   /
638                   /       ******************
639                   /                        **
640                           DECIMAL        /**
641                   /                        **
642                   /       ******************
643
644
645   14316   6277    PFXD1,  -833
646   14317   7771    PFXD2,  -7              /REMEMBER THE 0.10 INCH INSPECTOR
647                                           /START UP !!
648
649   14320   7355    PFMD1,  -275
650   14321   7773    PFMD2,  -5
651
652                           OCTAL
653
654
655   14322   0000    QUAPTR, 0               /CHANNEL DATA BASE ADDRESS POINTER.
656
657   14323   0000    QUERMG, ZBLOCK 3
```

```
658   14326   0000            0
659   14327   0000            0
660   14330   3563            TEXT "]3 PQI OVERSPEED"
661   14331   4020
662   14332   2111
663   14333   4017
664   14334   2605
665   14335   2223
666   14336   2005
667   14337   3504
668   14340   0000
669
670   14341   0000   QUMG1,   ZBLOCK 3          /MESSAGE TO BE SENT TO MEMORY.
671   14344   0000            0                 /WILL BE LAST SHEET MESSAGE
672
673   14372   7766
674   14373   0015
675   14374   3600
676   14375   0014
677   14376   7001
678   14377   7757
679           4400            PAGE
```

/ QUALITY SCREENING AND ZONING          PAL8-V10A 02/02/77   PAGE 29

```
680             /
681             /
682             /
683             /       FINISH THE SHEET BOOKKEEPING
684             /
685             /       COME HERE FROM "QUAL" OR "ZONE" WHEN THEY
686             /       ARE FINISHED, AND PUT THE QUALITY DECISION BACK
687             /       IN THE DATA TABLE. ALSO CLEAR THE SHEET ACTIVE
688             /       FLAG.
689             /
690             /
691   14400   7300   START2,  CLB
692   14401   4020            CAL
693   14402   0004            SUSPND
694
695   14403   1063            TAD CH1BAS        /GET THE "MSBW1" WORD FOR CHANNEL 1
696   14404   4777'           JMS GETDAT
697   14405   0017            MSBW1
698   14406   0376            AND (0377)        /SHOULDN'T NEED THIS, BUT ...
699   14407   7421            MQL               /SAVE IT FOR A MO.
700
701   14410   1066            TAD LASTQL        /GET THE CURRENT SHEET MESSAGE AND
702   14411   7510            SPA               /CHECK FOR SPECIAL MESSAGE. IF IT
703   14412   5215            JMP .+3           /IS, USE MSB'S FOR DATA, OTHERWISE
704   14413   7112            CLL RTR           /LEFT JUSTIFY IT - THE SHORT WAY.
705   14414   7012            RTR
706   14415   0375            AND (7000)        /WANT JUST THE QUALITY DATA.
707   14416   7501            MQA               /"OR" IT WITH THE PQI DATA, AND
708   14417   4774'           JMS PUTDAT        /PUT IT BACK IN THE DATA BUFFER.
709
710   14420   1066            TAD LASTQL        /GET THE SHEET QUALITY DECISION, AN
711   14421   0373            AND (1007)        /MASK OFF ANY SPECIAL MESSAGE BITS.
712   14422   3066            DCA LASTQL
713
714   14423   1052            TAD ZONECD        /ARE WE IN ZONING MODE ?
715   14424   7650            SNA CLA
716   14425   3066            DCA LASTQL        /NO, FORCE MESSAGE FOR "NO DATA".
717
718   14426   1372            TAD (SELF)        /WAKE UP THE SELF CHECK TASK.
719   14427   4020            CAL
720   14430   0003            RUN
721
722   14431   7300            CLB
723   14432   3053            DCA SHDONE        /CLEAR THE SHEET ACTIVE FLAG.
724   14433   7330            AC4000            /CLEAR BIT 0 - FOR LHN TIMING.
725   14434   6515            DBCD OR851
726   14435   5200            JMP START2        /NOW GO BACK TO SLEEP.
```

```
/ QUALITY SCREENING AND ZONING              PAL8-V10A 02/02/77  PAGE 30

727     /
728     /
729     /
730     /                        ZONING DEFINITIONS
731     /
732     /
733     /
734     /
735     /
736     /
737     /
738     /                             MACHINE
739     /                            DIRECTION
740     /
741     /                               **
742     /                              ****
743     /                             ******
744     /                            * **** *
745     /                              *  *
746     /                              *  *
747     /                              *  *
748     /                              *  *           LEADING EDGE
749     /                              *  *             OR FRONT
750     /
751     /              -------    *************************
752     /           I             *************************
753     /        MD I             **                     **
754     /           I             **                     **
755     /           I             **                     **
756     /           V             **                     **
757     /                         **      14 X 17        **      STENCIL
758     /                         **       SHEET         **       SIDE
759     /                         **                     **
760     /                         **                     **
761     /                         **                     **
762     /                         **                     **
763     /                         *************************
764     /                         *************************
765     /
766     /                                                  I
767     /                                                  I
768     /                                         XD       I
769     /                                      <-------I
770     /                                                  I
771     /                                                  I
772     /                                         STK      I
773     /                                      <-------I
774     /                                                  I
775     /
776     /

/ QUALITY SCREENING AND ZONING              PAL8-V10A 02/02/77  PAGE 31

777     /
778     /
779     /
780     /        FRONT TO BACK ZONES
781     /
782     /
783     /                            LEADING EDGE
784     /
785     /              *************************
786     /              *************************
787     /              **                     **
788     /              **                     **
789     /              **       ZONE A        **
790     /              **                     **
791     /              **----------------------**       STENCIL
792     /              **                     **        SIDE
793     /              **                     **
```

```
794  /                              **     ZONE B        **
795  /                              **                   **
796  /                              ******************************
797  /                              ******************************
798  /
799  /
800  /
801  /
802  /
803  /
804  /
805  /        SIDE TO SIDE ZONES
806  /
807  /                                                LEADING EDGE
808  /
809  /
810  /                              ******************************
811  /                              ******************************
812  /                              **         I         **
813  /                              ** ZONE B  I         **
814  /                              **         I         **
815  /                              **         I         **         STENCIL
816  /                              **         I         **         SIDE
817  /                              **         I         **
818  /                              **         I         **
819  /                              **         I ZONE A  **
820  /                              **         I         **
821  /                              ******************************
822  /                              ******************************
```

/ QUALITY SCREENING AND ZONING          PAL8-V10A 02/02/77  PAGE 32

```
823  /
824  /
825  /
826  /    ZONING PARAMTER VALUE RANGES
827  /
828  /
829  /
830  /    PARAMETER          NO              NORMAL
831  /                       DEFECT          RANGE
832  /                       (DECIMAL)       (DECIMAL)
833  /
834  /    XD1                2047            0 TO 900
835  /    XD2                0               0 TO 900
836  /
837  /    STK1               2047            0 TO 900
838  /    STK2               0               0 TO 900
839  /
840  /    MD1                0               0 TO 300
841  /    MD2                0               0 TO 300
842  /
843  /
844  /
845  /    MEASUREMENT RESOLUTION
846  /
847  /
848  /    MD = .050 INCHES    OR   20 DIVISIONS PER INCH
849  /    XD = .020 INCHES    OR   50 DIVISIONS PER INCH
850  /
851  /
852  /
853  /
854  /    IN THE LIMIT TABLES THAT FOLLOW, EITHER TWO
855  /    OR FOUR OF THE LIMITS ARE USED FOR A GIVEN
856  /    ZONING CODE. THE UNUSED DATA IS MARKED "NA"
857  /    AND IS ASSIGNED VALUES SO THAT THE TESTS
858  /    FALL THROUGH WITHOUT SETTING THEIR DEFECT
859  /    FLAGS IN "ZONES1". THE VALUE FOR AN UNUSED
860  /    "1" PARAMETERS (XD1,MD1,SK1) IS "-0". THE
861  /    VALUE FOR UNUSED "2" PARAMETERS (XD2,MD2,
862  /    SK2) IS "-2300".
863  /
```

```
864                    /       SIDE TO SIDE ZONING USES XD AND SK DATA
865                    /       ONLY, WHILE FRONT TO BACK ZONING USES
866                    /       ONLY MD DATA.
```

/ QUALITY SCREENING AND ZONING                PAL8-V10A 02/02/77  PAGE 33

```
867     /
868     /
869     /       TABLE OF DEFINED ZONING LIMITS
870     /
871     /
872     /       ZONING              FUNCTION
873     /       CODE
874     /
875     /          0
876     /          1              ZONING PATTERN #1
877     /          2              ZONING PATTERN #2
878     /          3              ZONING PATTERN #3
879     /
880     /          4              NO ZONING
881     /
882     /
883     /
884     /       *************
885     /            **
886     /          DECIMAL  /**
887     /            **
888     /       *************
889
890
891  14436  0177   ZONTBL, 64+32+16+8+4+2+1   /"ALL DEFECTS" MASK.
892  14437  0000           0
893  14440  0000           0                  /CODE "0"    NOT USEABLE !
894  14441  0000           0
895  14442  0000           0                  /USED TO FORCE A SHEET TO BE UN-
896  14443  0000           0                  /ZONEABLE IF ZONING MODE IS TURNED
897  14444  0000           0                  /OFF.
898
899  14445  0107           64+4+2+1           /RM, EF, SPL, ED.
900  14446  6460           -720    /XD1
901  14447  7554           -148    /XD2         CODE "1"        14 X 14
902  14450  0000           -0      /MD1  NA                     SIDE-SIDE
903  14451  4060           -2000   /MD2  NA
904  14452  6474           -708    /SK1         ZONING  O N L Y
905  14453  7540           -160    /SK2
906
907  14454  0107           64+4+2+1           /RM, EF, SPL, ED.
908  14455  6710           -568    /XD1
909  14456  7326           -298    /XD2         CODE "2"        11 X 14
910  14457  0000           -0      /MD1  NA                     SIDE-SIDE
911  14460  4060           -2000   /MD2  NA
912  14461  6724           -556    /SK1         ZONING  O N L Y
913  14462  7312           -310    /SK2
```

/ QUALITY SCREENING AND ZONING                PAL8-V10A 02/02/77  PAGE 34

```
914     /
915  14463  0047           32+4+2+1           /STK, EF, SPL, ED.
916  14464  0000           -0      /XD1  NA
917  14465  4060           -2000   /XD2  NA    CODE "3"        7 X 17
918  14466  7564           -140    /MD1                        FRONT-BACK
919  14467  7564           -140    /MD2
920  14470  0000           -0      /SK1  NA    ZONING  O N L Y
921  14471  4060           -2000   /SK2  NA
922
923  14472  0177           64+32+16+8+4+2+1   /ALL DEFECTS
924  14473  0000           -0      /XD1  NA
925  14474  4060           -2000   /XD2  NA    CODE "4"
926  14475  0000           -0      /MD1  NA
927  14476  4060           -2000   /MD2  NA
928  14477  0000           -0      /SK1  NA
929  14500  4060           -2000   /SK2  NA
930
```

```
931   14501  0107           64+4+2+1                /RM, EF, SPL, ED.
932   14502  6460           -720        /XD1
933   14503  7554           -148        /XD2        CODE "5"        14 X 14
934   14504  0000           -0          /MD1   NA                   SIDE-SIDE
935   14505  4060           -2000       /MD2   NA
936   14506  6474           -708        /SK1
937   14507  7540           -160        /SK2
938
939   14510  0107           64+4+2+1                /RM, EF, SPL, ED.
940   14511  6710           -568        /XD1
941   14512  7326           -298        /XD2        CODE "6"        11 X 14
942   14513  0000           -0          /MD1   NA                   SIDE-SIDE
943   14514  4060           -2000       /MD2   NA
944   14515  6724           -556        /SK1
945   14516  7312           -310        /SK2
946
947   14517  0047           32+4+2+1                /STK, EF, SPL, ED.
948   14520  0000           -0          /XD1   NA
949   14521  4060           -2000       /XD2   NA   CODE "7"        7 X 17
950   14522  7564           -140        /MD1                        FRONT-BACK
951   14523  7564           -140        /MD2
952   14524  0000           -0          /SK1   NA
953   14525  4060           -2000       /SK2   NA
954
955
956                         OCTAL
957
958   14572  0037
959   14573  1007
960   14574  4244
961   14575  7000
962   14576  0377
963   14577  4234
964          4600           PAGE
```

/ QUALITY SCREENING AND ZONING          PAL8-V10A 02/02/77 PAGE 35

```
965                /
966                /
967                /
968                /%RT   ZONE - DEFECT ZONING TASK
969                /
970                /      THIS TASK WILL DETERMINE IF THE DEFECT'S
971                /      POSITION ALLOWS RECLAIMING PART OF THE SHEET
972                /      UNDER THE CURRENT ZONING CODE.
973                /
974                /
975   14600  7300  START3, CLB
976   14601  4020          CAL
977   14602  0004          SUSPND          /JUST GO TO SLEEP TIL NEEDED.
978
979   14603  7300          CLB
980   14604  1052          TAD ZONECD      /COMPUTE THE ADDRESS OF THE ZONING
981   14605  7104          CLL RAL         /LIMITS FOR THIS ZONING CODE.
982   14606  1052          TAD ZONECD
983   14607  7104          CLL RAL
984   14610  1052          TAD ZONECD      /(ZONECD * 7)
985   14611  1377          TAD (ZONTBL)
986   14612  3351          DCA ZONPTR      /SAVE AS AN ADDRESS POINTER.
987
988   14613  1130          TAD SHSTAT      /CAN WE ZONE THIS SHEET ?
989   14614  0751          AND I ZONPTR    /MASK OUT UNZONEABLE DEFECTS.
990   14615  7640          SZA CLA
991   14616  5251          JMP ZONE1       /DEFECTS ARE PRESENT WE CAN'T HANDL
992
993   14617  3344          DCA NOTZA       /CLEAR THE NO-ZONE FLAGS.
994   14620  3345          DCA NOTZB
995
996   14621  1130          TAD SHSTAT      /ARE THERE ONLY SMALL DEFECTS ON
997   14622  0376          AND (7757)      /THIS SHEET ?
998   14623  7650          SNA CLA
999   14624  1132          TAD PFADJ       /YES, MOVE OFFSET FOR PICTURE FRAME
```

```
1000   14625   3346              DCA PPFADJ
1001   14626   1346              TAD PPFADJ      /ALSO CREATE MINUS OFFSET. NOTE:
1002   14627   7041              CIA             /IF OTHER THAN SMALL DEFECTS ARE
1003   14630   3347              DCA NPFADJ      /PRESENT, THIS NUMBER IS ZERO !!!!!
1004
1005   14631   1063              TAD CH1BAS      /GET THE BASE OF THE CHANNEL 1 DATA
1006   14632   4257              JMS ZONES1      /AND GO CHECK THE SHEET DATA
1007                                              /AGAINST THE ACTIVE ZONING LIMITS.
1008   14633   1064              TAD CH2BAS      /NOW DO THE SAME FOR CHANNEL 2.
1009   14634   4257              JMS ZONES1
1010   14635   1065              TAD CH3BAS      /AND CHANNEL 3.
1011   14636   4257              JMS ZONES1
```
/ QUALITY SCREENING AND ZONING          PAL8-V10A 02/02/77  PAGE 36

```
1012                  /
1013                  /
1014                  /
1015                  /         DETERMINE THE PROPER QUALITY MESSAGE
1016                  /
1017                  /
1018   14637   1344              TAD NOTZA       /IS ZONE "A" CLEAR ?
1019   14640   7640              SZA CLA
1020   14641   5244              JMP .+3
1021   14642   1375              TAD (1002)      /YES, SET THE "ZONE A" MESSAGE FOR
1022   14643   5252              JMP ZONE2       /THIS SHEET.
1023
1024   14644   1345              TAD NOTZB       /IS "ZONE B" CLEAR ?
1025   14645   7640              SZA CLA
1026   14646   5251              JMP .+3
1027   14647   1374              TAD (1003)      /YES, SET THE "ZONE B" MESSAGE FOR
1028   14650   5252              JMP ZONE2       /THIS SHEET.
1029
1030   14651   1373     ZONE1,   TAD (1004)      /BOTH ZONES CONTAIN A DEFECT, SAY SO
1031   14652   3066     ZONE2,   DCA LASTQL      /SAVE THE SHEET QUALITY MESSAGE.
1032   14653   1372              TAD (QFIN)      /NOW RUN THE "FINISH SHEET" TASK.
1033   14654   4020              CAL
1034   14655   0003              RUN
1035   14656   5200              JMP START3      /BACK TO SLEEP.
```
/ QUALITY SCREENING AND ZONING          PAL8-V10A 02/02/77  PAGE 37

```
1036                  /
1037                  /
1038                  /         THIS SUBROUTINE CHECKS THE ZONING DATA FOR AN
1039                  /         INSPECTOR CHANNEL AGAINST THE LIMITS IN THE
1040                  /         ZONING TABLE FOR THE CURRENT ZONING CODE.  THE
1041                  /         BASE ADDRESS OF THE INSPECTOR CHANNEL DATA FOR
1042                  /         THIS SHEET IS IN THE ACCUMULATOR WHEN CALLED.
1043                  /
1044                  /         THE ZONING TEST USED BELOW LOOKS FOR CLEAR AREAS
1045                  /         OF PRODUCT, EITHER ZONE "A" OR "B".  FOR EXAMPLE,
1046                  /         IF THE VALUE OF XD1 IS LESS THAN IT'S LIMIT,
1047                  /         ZONE "A" CONTAINS A DEFECT, BUT THIS DOES NOT
1048                  /         SAY ZONE "B" IS GOOD OR BAD.  IF XD1 EXCEEDS
1049                  /         THE ZONING BOUNDARY, ZONE "A" IS GOOD.  SIMILARLY,
1050                  /         XD2 IS USED TO CHECK ZONE "B".  IF THE VALUE OF
1051                  /         XD2 EXCEEDS IT'S LIMIT, ZONE "B" CONTAINS A
1052                  /         DEFECT, AND NOTHING IS SAID ABOUT ZONE "A".  IF
1053                  /         XD2 IS LESS THAN THE ZONING BOUNDARY, ZONE "B"
1054                  /         IS GOOD.
1055                  /
1056                  /
1057   14657   0000     ZONES1,  0
1058   14660   3350              DCA DATPTR      /SAVE THE CHANNEL DATA POINTER.
1059
1060   14661   7301              CLB IAC         /SET UP AN AUTO-INDEX FOR THE
1061   14662   1351              TAD ZONPTR      /ZONING LIMITS TO USE.
1062   14663   3352              DCA ZONPT2
1063
1064
1065   14664   1350              TAD DATPTR      /GET THE XD1 DATA FOR THIS CHANNEL.
1066   14665   4771'             JMS GETDAT
1067   14666   0006              XD1             /(XD1 DATA OFFSET.)
```

```
1068  14667  1346           TAD PPFADJ    /MAYBE ADD IN +PICTURE FRAME OFFSET
1069  14670  7510           SPA           /(WILL SKP IF THE +PICTURE FRAME WA
1070  14671  7350           AC3777        /ADDED TO THE XD1 OFF-SHEET VALUE.)
1071  14672  1752           TAD I ZONPT2  /COMPARE TO THE LIMIT
1072  14673  2352           ISZ ZONPT2
1073  14674  7710           SPA CLA
1074  14675  2344           ISZ NOTZA     /THERE IS A DEFECT IN ZONE A !
1075
1076
1077  14676  1350           TAD DATPTR    /GET THE XD2 DATA
1078  14677  4771'          JMS GETDAT
1079  14700  0007           XD2
1080  14701  1347           TAD NPFADJ    /MAYBE ADD IN -PICTURE FRAME OFFSET
1081  14702  7500           SMA           /(WILL SKP IF THE -PICTURE FRAME WA
1082                                      /ADDED TO THE XD2 OFF-SHEET VALUE.)
1083  14703  1752           TAD I ZONPT2  /COMPARE TO THE LIMIT.
1084  14704  2352           ISZ ZONPT2
1085  14705  7700           SMA CLA
1086  14706  2345           ISZ NOTZB     /THERE IS A DEFECT IN ZONE B.
```

/ QUALITY SCREENING AND ZONING           PAL8-V10A 02/02/77  PAGE 38

```
1087                /
1088  14707  1350           TAD DATPTR    /GET THE MD1 DATA.
1089  14710  4771'          JMS GETDAT
1090  14711  0010           MD1
1091  14712  7440           SZA           /ZERO IS OFF SHEET - NO DEFECT.
1092  14713  1752           TAD I ZONPT2  /COMPARE TO THE LIMIT
1093  14714  2352           ISZ ZONPT2
1094  14715  7710           SPA CLA
1095  14716  2344           ISZ NOTZA     /THERE IS A DEFECT IN ZONE A.
1096
1097  14717  1350           TAD DATPTR    /GET THE MD2 DATA
1098  14720  4771'          JMS GETDAT
1099  14721  0011           MD2
1100  14722  1752           TAD I ZONPT2  /COMPARE TO THE LIMIT.
1101  14723  2352           ISZ ZONPT2
1102  14724  7700           SMA CLA
1103  14725  2345           ISZ NOTZB     /THERE IS A DEFECT IN ZONE B.
1104
1105  14726  1350           TAD DATPTR    /GET THE STK1 DATA
1106  14727  4771'          JMS GETDAT
1107  14730  0014           STK1
1108  14731  1752           TAD I ZONPT2  /COMPARE TO THE LIMIT
1109  14732  2352           ISZ ZONPT2
1110  14733  7710           SPA CLA
1111  14734  2344           ISZ NOTZA     /THERE IS A DEFECT IN ZONE A.
1112
1113  14735  1350           TAD DATPTR    /AND NOW DO STK2.
1114  14736  4771'          JMS GETDAT
1115  14737  0030           STK2
1116  14740  1752           TAD I ZONPT2  /COMPARE TO THE LIMIT.
1117  14741  7700           SMA CLA
1118  14742  2345           ISZ NOTZB     /THERE IS A DEFECT IN ZONE B.
1119
1120  14743  5657           JMP I ZONES1  /THIS CHANNEL IS DONE, RETURN.
1121
1122
1123  14744  0000   NOTZA,  0             /DEFECT IN ZONE A FLAG.
1124  14745  0000   NOTZB,  0             /DEFECT IN ZONE B FLAG.
1125  14746  0000   PPFADJ, 0             /+ PICTURE FRAME OFFSET (SD ONLY!).
1126  14747  0000   NPFADJ, 0             /- PICTURE FRAME OFFSET (SD ONLY!).
1127  14750  0000   DATPTR, 0             /BASE ADDRESS OF INSPECTOR DATA.
1128  14751  0000   ZONPTR, 0             /POINTER TO CURRENT ZONING LIMITS.
1129  14752  0000   ZONPT2, 0             /WORKING POINTER TO ZONING LIMITS.
```

/ QUALITY SCREENING AND ZONING           PAL8-V10A 02/02/77  PAGE 39

```
1130                /
1131
1132  14771  4234
1133  14772  0015
1134  14773  1004
```

```
1135    14774   1003
1136    14775   1002
1137    14776   7757
1138    14777   4436
1139            5000            PAGE
1140
1141                    $=$=LHN=$=$
```

/ QUALITY SCREENING AND ZONING          PAL8-V10A 02/02/77   PAGE 40

| | | | | | | | |
|---|---|---|---|---|---|---|---|
| ACL | 7701 | COMMAN | 0043 | HGHFLD | 0030 | NULLLO | 3500 |
| ACS | 7403 | CONDAT | 0051 | IND | 1000 | NUMDEF | 0013 |
| AC0002 | 7326 | CUR | 0010 | INITZE | 0033 | OSDSKD | 0004 |
| AC2000 | 7332 | CURSAM | 0044 | INIWT | 0000 | OSFILL | 0000 |
| AC3777 | 7350 | CUR2 | 0010 | INIWT2 | 0000 | OSFLDS | 0002 |
| AC4000 | 7330 | CUR3 | 0010 | INIWT3 | 0000 | OSKBDV | 0003 |
| AC5777 | 7352 | DAD | 7443 | INIWT4 | 0000 | OSSYSD | 0011 |
| AC7775 | 7346 | DATBAS | 2000 | ISTATU | 0012 | OSTTDV | 0004 |
| AC7776 | 7344 | DATCFL | 0013 | KBDEV | 0003 | OS8F | 0016 |
| AC7777 | 7340 | DATCLO | 1400 | KL8A | 0000 | OS8FFL | 0000 |
| AIR0 | 0010 | DATCPG | 0110 | KL8ALI | 0100 | OS8FLD | 0000 |
| AIR1 | 0011 | DATDEV | 0011 | LASTQL | 0066 | OS8FLO | 6200 |
| AIR2 | 0012 | DATE | 0040 | LDPKN | 0027 | OS8FPG | 0160 |
| AIR3 | 0013 | DATFLD | 0020 | LDPKP | 0026 | OS8HPR | 0071 |
| AIR4 | 0014 | DATLEN | 4000 | LOGN | 0026 | OS8LOC | 4600 |
| AIR5 | 0015 | DATPTR | 4750 | LPT | 0035 | OS8PGZ | 0166 |
| AIR6 | 0016 | DBCI | 6003 | LPTFLD | 0030 | OWNTTY | 0072 |
| AIR7 | 0017 | DBCO | 6005 | LPTLOC | 3200 | PARTNS | 0000 |
| ALGO | 0013 | DBDI | 6000 | LSR | 7417 | PDP12 | 0000 |
| ALGOFL | 0010 | DBEI | 6001 | LSTFLG | 0001 | PDP8E | 0001 |
| ALGOLO | 5000 | DBRI | 6004 | MARKTI | 0000 | PERIOD | 2000 |
| ALGOPG | 0140 | DBRO | 6007 | MCR | 0036 | PFADJ | 0132 |
| ASR | 7415 | DBSK | 6002 | MCRCDV | 0034 | PFMD1 | 4320 |
| ASSGN | 0200 | DBSO | 6006 | MCRCLK | 0001 | PFMD2 | 4321 |
| BLKARG | 0010 | DB8FLD | 0013 | MCRDMP | 0001 | PFXD1 | 4316 |
| BUFFLD | 0020 | DB8LOC | 0200 | MCREF | 0070 | PFXD2 | 4317 |
| BUFLEN | 1000 | DB8PGZ | 0100 | MCRFLD | 0030 | PIAT | 0023 |
| BUF1AD | 6000 | DCM | 7575 | MCRLOC | 0200 | PLDMDN | 0005 |
| BUF2AD | 7000 | DEBWT | 0004 | MCRPGZ | 0150 | PLDMDP | 0003 |
| CAL | 4020 | DECODE | 0010 | MCRSYS | 0001 | PLDXDN | 0004 |
| CAM | 7621 | DERAIL | 0007 | MDMAX | 0032 | PLDXDP | 0002 |
| CANCEL | 7000 | DLD | 7663 | MD1 | 0010 | POST | 0005 |
| CDI | 6203 | DNEWT | 0001 | MD2 | 0011 | POSTDS | 5424 |
| CHECKP | 0000 | DPIC | 7573 | MEMDAT | 0046 | PPFADJ | 4746 |
| CHECKW | 0037 | DPSZ | 7451 | MIS1FL | 0020 | PQIVER | 6402 |
| CH1BAS | 0063 | DR8 | 0003 | MIS1LO | 0200 | PSDMD | 0001 |
| CH1DAT | 0004 | DR8FLD | 0010 | MSBW1 | 0017 | PSDXD | 0000 |
| CH1EFG | 0054 | DR8LOC | 1200 | MSBW2 | 0021 | PUTDAT | 4244 |
| CH1OFL | 0057 | DR8S1 | 0510 | MSGTBL | 1376 | PWRCLR | 3200 |
| CH2ADJ | 0134 | DST | 7445 | MSGWT | 0020 | PWRF | 0002 |
| CH2BAS | 0064 | DUMP | 0031 | MUY | 7405 | PWRFAL | 0001 |
| CH2DAT | 0005 | DVI | 7407 | NETWT | 0010 | PWRFFL | 0000 |
| CH2EFG | 0055 | EAE | 0001 | NEWR | 0020 | PWRFLO | 3000 |
| CH2OFL | 0060 | EFPKN | 0036 | NIAT | 0024 | QFIN | 0015 |
| CH2SCF | 0133 | EFPKP | 0035 | NMI | 7411 | QUAL | 0012 |
| CH3BAS | 0065 | EFWT | 2000 | NOCRLF | 2000 | QUALFL | 0010 |
| CH3DAT | 0006 | EMULFT | 0015 | NOLINE | 0400 | QUALLO | 3600 |
| CH3EFG | 0056 | ENABWT | 0040 | NONRWT | 4000 | QUALPG | 0130 |
| CH3LOC | 0041 | EORMWT | 0200 | NOPACK | 4000 | QUALSA | 4270 |
| CH3OFL | 0061 | FBTTY | 0000 | NOTZA | 4744 | QUALSB | 4277 |
| CLB | 7300 | FCLO | 0017 | NOTZB | 4745 | QUALSC | 4314 |
| CLKQLN | 0010 | FIMQDY | 0373 | NPFADJ | 4747 | QUALS1 | 4252 |
| CLKTYP | 0000 | FREE | 4000 | NTASKS | 0037 | QUAL1 | 3624 |
| CLOCK | 0001 | GETDAT | 4234 | NULL | 0040 | QUAL2 | 3700 |
| COMM | 0027 | HERTZ | 0170 | NULLFL | 0000 | QUAL3 | 3702 |

/ QUALITY SCREENING AND ZONING          PAL8-V10A 02/02/77   PAGE 40-1

| | | | |
|---|---|---|---|
| QUAL4 | 3720 | STK2 | 0030 |
| QUAL4A | 4000 | STPKN | 0034 |
| QUAL4B | 4016 | STPKP | 0033 |
| QUAL4C | 4035 | SUSPND | 0004 |
| QUAL4D | 4053 | SWAB | 7431 |

| | | | | | | | | |
|---|---|---|---|---|---|---|---|---|
| QUAL5 | 4200 | SWBA | 7447 | | | | | |
| QUAL6 | 4221 | SWPWT | 0400 | | | | | |
| QUAL7 | 4226 | TALK | 0007 | | | | | |
| QUAPTR | 4322 | TASK | 0012 | | | | | |
| QUERMG | 4323 | TASK2 | 0015 | | | | | |
| QUMG1 | 4341 | TASK3 | 0014 | | | | | |
| QUSCR | 0131 | TFTABL | 1677 | | | | | |
| RECEIV | 0001 | TIMOUT | 2000 | | | | | |
| RESCHD | 0013 | TODH | 0037 | | | | | |
| RK8E | 0011 | TODL | 0036 | | | | | |
| RK8EFL | 0000 | TOTNA | 0020 | | | | | |
| RK8ELO | 3200 | TOTPA | 0016 | | | | | |
| ROLLIN | 0040 | TRY | 0032 | | | | | |
| RUN | 0003 | TSTABL | 1474 | | | | | |
| RUNWT | 1000 | TSWFLG | 0035 | | | | | |
| SAM | 7457 | TTDEV | 0004 | | | | | |
| SAMLOC | 0045 | TTY | 0034 | | | | | |
| SAMNUM | 0043 | TTYFLD | 0000 | | | | | |
| SAMP | 0021 | TTYLOC | 3600 | | | | | |
| SAMPFL | 0010 | TTYS | 0025 | | | | | |
| SAMPLO | 2400 | TTYSFL | 0020 | | | | | |
| SAMREC | 0042 | TTYSLO | 0600 | | | | | |
| SCA | 7441 | UNBARG | 0012 | | | | | |
| SCHEDU | 1000 | USERWT | 0100 | | | | | |
| SCL | 7403 | VERS | 0001 | | | | | |
| SDAUTO | 0022 | VERS2 | 0001 | | | | | |
| SDPK | 0025 | VERS3 | 0001 | | | | | |
| SELDAT | 0050 | VERS4 | 0000 | | | | | |
| SELF | 0037 | WAITE | 0002 | | | | | |
| SELFFL | 0030 | WAITM | 4425 | | | | | |
| SELFLO | 4000 | WAITX | 0014 | | | | | |
| SELFPG | 0100 | XDMAX | 0031 | | | | | |
| SEND | 0000 | XD1 | 0006 | | | | | |
| SENDW | 0011 | XD2 | 0007 | | | | | |
| SHDONE | 0053 | XODFLD | 0030 | | | | | |
| SHERTZ | 0170 | XODLOC | 6200 | | | | | |
| SHL | 7413 | ZERO | 0039 | | | | | |
| SHSTAT | 0130 | ZONE | 0014 | | | | | |
| SHTCNT | 0047 | ZONECD | 0352 | | | | | |
| SHUTOP | 0062 | ZONES1 | 4657 | | | | | |
| SKB | 7471 | ZONE1 | 4651 | | | | | |
| SKPINS | 0006 | ZONE2 | 4652 | | | | | |
| SKPOUT | 0016 | ZONPTR | 4751 | | | | | |
| SNAP | 0024 | ZONPT2 | 4752 | | | | | |
| SNAPFL | 0020 | ZONTBL | 4436 | | | | | |
| SNAPLO | 1200 | | | | | | | |
| START | 3600 | | | | | | | |
| START2 | 4400 | | | | | | | |
| START3 | 4600 | | | | | | | |
| STK1 | 0014 | | | | | | | |

ERRORS DETECTED: 0
LINKS GENERATED: 38

| | | | | | | | | |
|---|---|---|---|---|---|---|---|---|
| ACL | 348 | 387 | 403 | 418 | 439 | 453 | 468 | |
| AC3777 | 1070 | | | | | | | |
| AC4000 | 225 | 724 | | | | | | |
| CAL | 218 | 238 | 251 | 531 | 542 | 692 | 719 | 976 | 1033 |
| CHECKW | 121# | 287 | 293 | 299 | | | | |
| CH1BAS | 268 | 285 | 310 | 512 | 695 | 1005 | | |
| CH2ADJ | 73# | 349 | 388 | 404 | 419 | 440 | 454 | 469 |
| CH2BAS | 273 | 291 | 314 | 336 | 377 | 391 | 408 | 427 | 442 | 457 |
| | 515 | 1008 | | | | | | |
| CH2SCF | 71# | 345 | 384 | 400 | 415 | 432 | 447 | 462 |
| CH3BAS | 278 | 297 | 319 | 518 | 1010 | | | |
| CH3LOC | 264 | 269 | 274 | | | | | |
| CLB | 217 | 227 | 242 | 256 | 376 | 407 | 477 | 504 | 529 | 575 |
| | 691 | 722 | 975 | 979 | 1060 | | | |
| CUR | 10 | 18 | 52# | 56 | 63 | 562 | 574 | |
| CUR2 | 20 | 20 | 56# | 60 | | | | |

| | | | | | | | | | |
|---|---|---|---|---|---|---|---|---|---|
| CUR3 | 30 | 30 | 60# | | | | | | |
| DATBAS | 267 | 272 | 277 | | | | | | |
| DATFLD | 560 | 572 | | | | | | | |
| DATPTR | 1058 | 1065 | 1077 | 1088 | 1097 | 1105 | 1113 | 1127# | |
| DBCO | 725 | | | | | | | | |
| DBSO | 226 | | | | | | | | |
| DRB51 | 226 | 725 | | | | | | | |
| DVI | 346 | 385 | 401 | 416 | 434 | 449 | 464 | | |
| EFPKN | 120# | | | | | | | | |
| EFPKP | 119# | | | | | | | | |
| EMULFT | 101# | | | | | | | | |
| GETDAT | 286 | 292 | 298 | 311 | 315 | 320 | 337 | 378 | 392 | 429 |
| | 428 | 443 | 458 | 556# | 557 | 558 | 559 | 561 | 563 | 573 |
| | 589 | 596 | 603 | 615 | 622 | 696 | 1066 | 1078 | 1089 | 1098 |
| | 1106 | 1114 | | | | | | | | |
| INIWT | 15 | 53# | | | | | | | |
| INIWT2 | 25 | 57# | | | | | | | |
| INIWT3 | 35 | 61# | | | | | | | |
| ISTATU | 98# | 312 | 316 | 321 | | | | | |
| LASTQL | 243 | 246 | 250 | 539 | 701 | 710 | 712 | 716 | 1031 |
| LDPKN | 112# | | | | | | | | |
| LDPKP | 111# | | | | | | | | |
| MDMAX | 116# | 604 | | | | | | | |
| MD1 | 96# | 616 | 1090 | | | | | | |
| MD2 | 97# | 623 | 1099 | | | | | | |
| MSBW1 | 103# | 697 | | | | | | | |
| MSBW2 | 106# | | | | | | | | |
| MSGTBL | 7 | 17 | 27 | | | | | | |
| MUY | 344 | 383 | 399 | 414 | 431 | 446 | 461 | | |
| NIAT | 109# | | | | | | | | |
| NOTZA | 993 | 1018 | 1074 | 1095 | 1111 | 1123# | | | |
| NOTZB | 994 | 1024 | 1086 | 1103 | 1118 | 1124# | | | |
| NPFADJ | 1003 | 1080 | 1126# | | | | | | |
| NUMDEF | 99# | | | | | | | | |
| PFADJ | 70# | 999 | | | | | | | |
| PFMD1 | 617 | 649# | | | | | | | |
| PFMD2 | 624 | 650# | | | | | | | |
| PFX01 | 591 | 645# | | | | | | | |
| PFX02 | 598 | 646# | | | | | | | |
| PIAT | 108# | | | | | | | | |
| PLDMDN | 92# | | | | | | | | |
| PLDMDP | 90# | | | | | | | | |
| PLDXDN | 91# | 459 | | | | | | | |
| PLDXDP | 89# | 444 | | | | | | | |
| PPFADJ | 1000 | 1001 | 1068 | 1125# | | | | | |
| PSDMD | 88# | | | | | | | | |
| PSDXD | 87# | 429 | | | | | | | |
| PUTDAT | 350 | 389 | 405 | 420 | 441 | 455 | 470 | 571# | 576 | 708 |
| QFIN | 55 | 541 | 1032 | | | | | | |
| QUAL | 51 | | | | | | | | |
| QUALFL | 52 | | | | | | | | |
| QUALLO | 76 | | | | | | | | |
| QUALPG | 65 | | | | | | | | |
| QUALSA | 593 | 602# | | | | | | | |
| QUALSB | 600 | 613# | | | | | | | |
| QUALSC | 619 | 628# | | | | | | | |
| QUALS1 | 513 | 516 | 519 | 585# | 607 | 611 | 613 | 626 | 628 | 629 |
| QUAL1 | 232 | 246# | | | | | | | |
| QUAL2 | 290 | 296 | 303# | | | | | | |
| QUAL3 | 302 | 310# | | | | | | | |
| QUAL4 | 335# | | | | | | | | |
| QUAL4A | 341 | 351 | 376# | | | | | | |
| QUAL4B | 381 | 391# | | | | | | | |
| QUAL4C | 396 | 407# | | | | | | | |
| QUAL4D | 412 | 427# | | | | | | | |
| QUAL5 | 486 | 504# | | | | | | | |
| QUAL6 | 505 | 510 | 514 | 517 | 520 | 529# | | | |
| QUAL7 | 304 | 488 | 522 | 539# | | | | | |
| QUAPTR | 586 | 588 | 595 | 602 | 614 | 621 | 655# | | |
| QUERMG | 235 | 241 | 657# | | | | | | |
| QUMG1 | 229 | 249 | 254 | 670# | | | | | |
| QUSCR | 69# | | | | | | | | |
| RUN | 532 | 543 | 720 | 1034 | | | | | |

| | | | | | | | | | |
|---|---|---|---|---|---|---|---|---|---|
| SDAUTO | 107# | | | | | | | | |
| SDPK | 110# | | | | | | | | |
| SELF | 718 | | | | | | | | |
| SEND | 239 | 252 | | | | | | | |
| SHDONE | 228 | 233 | 257 | 723 | | | | | |
| SHSTAT | 67# | 323 | 484 | 507 | 988 | 996 | | | |
| START | 11 | 217# | 533 | 544 | | | | | |
| START2 | 21 | 691# | 726 | | | | | | |
| START3 | 31 | 975# | 1035 | | | | | | |
| STK1 | 100# | 393 | 1107 | | | | | | |
| STK2 | 114# | 410 | 1115 | | | | | | |
| STPKN | 118# | | | | | | | | |
| STPKP | 117# | | | | | | | | |
| SUSPND | 219 | 693 | 977 | | | | | | |
| SWAB | 335 | | | | | | | | |
| TALK | 253 | | | | | | | | |
| TASK | 7 | 9 | 14 | 51# | | | | | |
| TASK2 | 17 | 19 | 24 | 55# | | | | | |
| TASK3 | 27 | 29 | 34 | 59# | | | | | |
| TFTABL | 14 | 24 | 34 | | | | | | |
| TOTNA | 105# | | | | | | | | |
| TOTPA | 102# | | | | | | | | |
| TSTABL | 9 | 19 | 29 | | | | | | |
| TTYS | 240 | | | | | | | | |
| VERS | 13 | 38# | | | | | | | |
| VERS2 | 23 | 39# | | | | | | | |
| VERS3 | 33 | 40# | | | | | | | |
| XDMAX | 115# | | | | | | | | |
| XD1 | 93# | 338 | 590 | 1067 | | | | | |
| XD2 | 94# | 379 | 597 | 1079 | | | | | |
| ZONE | 59 | 530 | | | | | | | |
| ZONECD | 714 | 980 | 982 | 984 | | | | | |
| ZONES1 | 1006 | 1009 | 1011 | 1057# | 1120 | | | | |
| ZONE1 | 991 | 1030# | | | | | | | |
| ZONE2 | 1022 | 1028 | 1031# | | | | | | |
| ZONPTR | 986 | 989 | 1061 | 1128# | | | | | |
| ZONPT2 | 1062 | 1071 | 1072 | 1083 | 1084 | 1092 | 1093 | 1100 | 1101 | 1108 |
| | 1109 | 1116 | 1129# | | | | | | |
| ZONTBL | 891# | 985 | | | | | | | |
| 013763 | 347 | | | | | | | | |
| 013767 | 275 | | | | | | | | |
| 013770 | 270 | | | | | | | | |
| 013771 | 267 | 272 | 277 | | | | | | |
| 013772 | 266 | 271 | 276 | | | | | | |
| 013773 | 265 | | | | | | | | |
| 013775 | 248 | 303 | | | | | | | |
| 014173 | 487 | | | | | | | | |
| 014176 | 386 | 402 | 417 | 435 | 450 | 465 | | | |
| 014372 | 605 | | | | | | | | |
| 014373 | 541 | | | | | | | | |
| 014375 | 530 | | | | | | | | |
| 014376 | 521 | | | | | | | | |
| 014377 | 508 | | | | | | | | |
| 014572 | 718 | | | | | | | | |
| 014573 | 711 | | | | | | | | |
| 014575 | 706 | | | | | | | | |
| 014576 | 698 | | | | | | | | |
| 014772 | 1032 | | | | | | | | |
| 014773 | 1030 | | | | | | | | |
| 014774 | 1027 | | | | | | | | |
| 014775 | 1021 | | | | | | | | |
| 014776 | 997 | | | | | | | | |
| 014777 | 985 | | | | | | | | |

V4

We claim:

1. An apparatus for obtaining sheet product from a web running at on-line speeds including inspection means for determining the existence and location of anomalies in said web and generating corresponding anomaly output signals, classifying means responsive to said anomaly output signals for classifying, by generating reject signals, preselected rectangular areas of said web as acceptable or rejectable; means for chopping said web into sheets of said preselected areas, and means responsive to said reject signals for segregating said unacceptable sheets from said acceptable sheets, the improvement wherein:

said classifying means including logic means responsive to said anomaly output signals for generating region signals defining a closed region containing all of said anomalies in each said preselected area, and computer means for comparing said region signals with reference signals defining acceptable product to classify said preselected areas as acceptable or rejectable for optimizing the yield of sheet product.

2. The apparatus set forth in claim 1 wherein said logic means selects said anomaly location signals corresponding to the smallest rectangularly shaped region in each preselected area which contains all detected anomalies.

3. The apparatus set forth in claim 2 wherein said logic means separately processes anomaly signals corresponding to the transverse location of streaks and other defects; and to the longitudinal location of said other defects.

4. The apparatus set forth in claim 3 wherein said computer means includes programming means for selecting zones in each of said preselected areas according to available product size, quality and cost per sheet.

5. The apparatus set forth in claim 4 wherein said computer means responds to said anomaly locations corresponding to longitudinal defect locations to define zones front-to-back longitudinally of said web.

6. The apparatus set forth in claim 5 wherein said computer means responds to said anomaly locations corresponding to transverse defect locations to define zones side-to-side transversely of said web.

7. The apparatus set forth in claim 6 wherein said computer means responds to said anomaly locations by expecting borders of said region of substantial width.

* * * * *